United States Patent
Reese

(10) Patent No.: US 9,874,431 B2
(45) Date of Patent: Jan. 23, 2018

(54) ANGULAR DISPLACEMENT SENSOR OF COMPLIANT MATERIAL

(71) Applicant: Bend Labs, Inc., South Salt Lake City, UT (US)

(72) Inventor: Shawn P. Reese, Salt Lake City, UT (US)

(73) Assignee: Bend Labs, Inc., South Salt Lake City, UT (US)

( * ) Notice: Subject to any disclaimer, the term of this patent is extended or adjusted under 35 U.S.C. 154(b) by 0 days.

(21) Appl. No.: 15/270,649

(22) Filed: Sep. 20, 2016

(65) Prior Publication Data

US 2017/0074637 A1 Mar. 16, 2017

Related U.S. Application Data

(60) Continuation of application No. 14/881,057, filed on Oct. 12, 2015, now Pat. No. 9,476,692, which is a
(Continued)

(51) Int. Cl.
*G01B 7/16* (2006.01)
*G01B 7/30* (2006.01)
(Continued)

(52) U.S. Cl.
CPC .............. *G01B 7/22* (2013.01); *A61B 5/1071* (2013.01); *A61B 5/6801* (2013.01); *G01B 7/003* (2013.01);
(Continued)

(58) Field of Classification Search
None
See application file for complete search history.

(56) References Cited

U.S. PATENT DOCUMENTS 4,442,606 A 4/1984 Graham et al.
4,542,291 A 9/1985 Zimmerman
(Continued)

FOREIGN PATENT DOCUMENTS

EP 0287149 A2 10/1988

OTHER PUBLICATIONS

Pelrine, Ronald E., Roy D. Combluh, and Jose P. Joseph. "Electrostriction of polymer dielectrics with compliant electrodes as a means of actuation." Sensors and Actuators A: Physical 64. 1 (1998): 77-85.
(Continued)

*Primary Examiner* — Jermele M Hollington
*Assistant Examiner* — Suresh K Rajaputra
(74) *Attorney, Agent, or Firm* — Lowenstein Sandler LLP

(57) ABSTRACT

Disclosed is an apparatus including a compliant capacitor and an elongated structure extending between a first end and a second end. The elongated structure is compliant material that is flexible and bendable from a linear, non-bent position to multiple bendable positions and is an elastomer based material. The compliant capacitor includes a first conductive filler embedded within and extending from the first end to the second end along a longitudinal length of the elongated structure to form a first electrode of the compliant capacitor. The compliant capacitor also includes a second conductive filler embedded within and extending from the first end to the second end along the longitudinal length to form a second electrode of the compliant capacitor. The compliant capacitor further includes an elastomer dielectric layer extending between the first conductive filler and the second conductive filler.

15 Claims, 17 Drawing Sheets

Related U.S. Application Data division of application No. 14/511,073, filed on Oct. 9, 2014, now Pat. No. 9,222,764, which is a continuation of application No. 14/460,726, filed on Aug. 15, 2014, now Pat. No. 8,941,392.

(60) Provisional application No. 62/003,030, filed on May 27, 2014, provisional application No. 61/867,047, filed on Aug. 17, 2013.

(51) Int. Cl.
  *G01L 1/14* (2006.01)
  *G01B 7/00* (2006.01)
  *A61B 5/107* (2006.01)
  *A61B 5/00* (2006.01)

(52) U.S. Cl.
  CPC ............. *G01B 7/30* (2013.01); *G01L 1/142* (2013.01); *A61B 2562/0261* (2013.01)

(56) References Cited

U.S. PATENT DOCUMENTS

| | | | |
|---|---|---|---|
| 4,897,927 A | 2/1990 | Nicol | |
| 5,047,719 A | 9/1991 | Johnson et al. | |
| 5,047,952 A | 9/1991 | Kramer et al. | |
| 5,086,785 A | 2/1992 | Gentile et al. | |
| 5,583,476 A | 12/1996 | Langford | |
| 5,610,528 A | 3/1997 | Neely et al. | |
| 6,127,672 A | 10/2000 | Danisch | |
| 6,389,187 B1 | 5/2002 | Greenaway et al. | |
| 6,575,041 B2 | 6/2003 | Schwarz et al. | |
| 6,809,462 B2 | 10/2004 | Pelrine et al. | |
| 7,249,422 B2 | 7/2007 | Bergamasco et al. | |
| 7,373,721 B2 | 5/2008 | Bergamasco et al. | |
| 7,395,717 B2 | 7/2008 | DeAngelis et al. | |
| 7,661,309 B2 | 2/2010 | Lan et al. | |
| 7,958,789 B2 | 6/2011 | Hayakawa et al. | |
| 7,984,659 B2 | 7/2011 | Fujimoto et al. | |
| 8,063,631 B2 | 11/2011 | Fermon et al. | |
| 8,232,797 B2 | 7/2012 | Decitre | |
| 8,451,011 B2 | 5/2013 | Hayakawa et al. | |
| 8,866,472 B2 | 10/2014 | Decitre et al. | |
| 8,941,392 B1* | 1/2015 | Reese | A61B 5/1071 324/658 |
| 9,113,663 B2 | 8/2015 | Stern | |
| 9,222,764 B2* | 12/2015 | Reese | A61B 5/1071 |
| 9,476,692 B2* | 10/2016 | Reese | A61B 5/1071 |
| 2002/0088931 A1 | 7/2002 | Danisch et al. | |
| 2005/0007106 A1 | 1/2005 | Goldfine et al. | |
| 2005/0101887 A1 | 5/2005 | Stark et al. | |
| 2006/0015191 A1 | 1/2006 | Bergamasco et al. | |
| 2006/0130347 A1 | 6/2006 | Bergamasco et al. | |
| 2008/0007253 A1 | 1/2008 | Takahata | |
| 2009/0015270 A1 | 1/2009 | Hayakawa et al. | |
| 2009/0085444 A1 | 4/2009 | Alvarez Icaza Rivera et al. | |
| 2009/0206831 A1 | 8/2009 | Fermon et al. | |
| 2010/0033196 A1 | 2/2010 | Hayakawa et al. | |
| 2010/0078999 A1 | 4/2010 | Celenza et al. | |
| 2010/0101329 A1 | 4/2010 | Berris, Jr. | |
| 2010/0109658 A1 | 5/2010 | Decitre | |
| 2010/0286950 A1 | 11/2010 | Heijkants et al. | |
| 2011/0232390 A1 | 9/2011 | Matsumoto et al. | |
| 2012/0019239 A1 | 1/2012 | Decitre | |
| 2012/0078999 A1 | 3/2012 | Andrew et al. | |
| 2012/0220904 A1 | 8/2012 | Warren | |
| 2012/0277531 A1 | 11/2012 | Krattiger et al. | |

OTHER PUBLICATIONS

Bose, Dr. Holger "Highly flexible mechanical sensors made of dielectric elastomers" Fraunhofer Institute for Silicate Research ISC, 2014 www.isc.Fraunhofer.de (2 pages).

Engel, Jonathan M., et al. "Multi-layer Embedment of Conductive and Non-Conductive PDMS for All-Elastomers MEMS" The 12th Solid State Sensors, Actuator, and Microsystem workshop, Hilton Head Island, SC, Jun. 2006 (4 pages).

Lipomi, Darren J., et al. "Skin-like pressure and strain sensors based on transparent elastic films of carbon nanotubes" Nature Nanotechnology Oct. 2011 (5 pages).

Cai, Lee, et al. "Super-stretchable, Transparent Carbon Nanotibe-Based Capacitive Strain Sensors for Juman Motion Detection" Scientific Reports, Oct. 2013 (9 pages).

Cohen, Daniel J., et al. "A Highly Elastic, Capacitive Strain Gauge Based on Percolating Nanotube Networks" American Chemical Society, Nano Letter, Mar. 2012 (5 pages).

Yao, Shanshan and Yong, Zhu "Wearable multifunctional sensors using printed stretchable conductors made of silver nanowires" Royal Society of Chemistry, Dec. 2013 (8 pages).

International Search Report and Written Opinion for PCT/US14/51535 dated Dec. 24, 2014.

Supplemental European Search Report for application No. EP14838435.7 dated Jul. 5, 2016.

\* cited by examiner

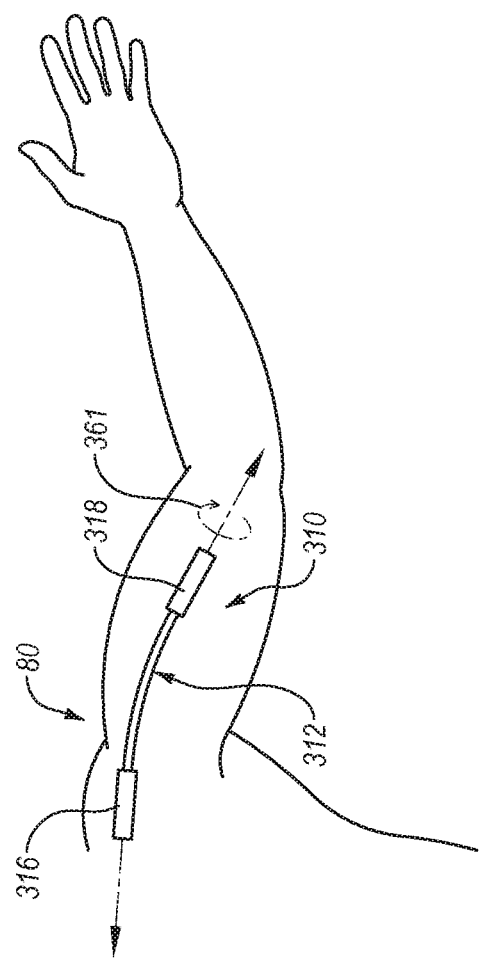
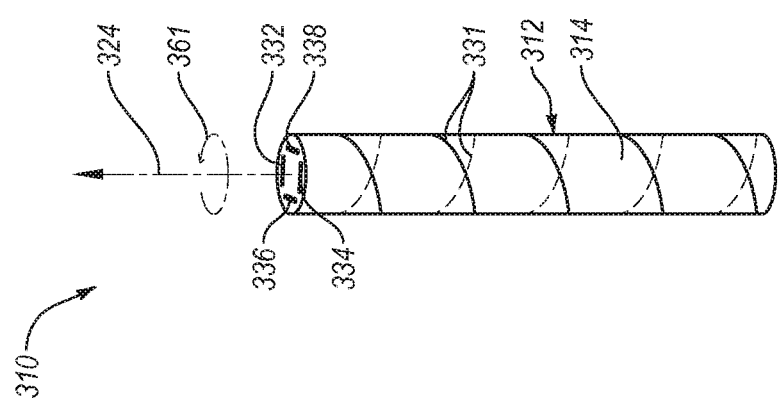
Fig. 10B
Fig. 10A

ANGULAR DISPLACEMENT SENSOR OF COMPLIANT MATERIAL

RELATED APPLICATIONS

This application is a continuation of U.S. application Ser. No. 14/881,057 filed Oct. 12, 2015, which is a divisional of U.S. application Ser. No. 14/511,073 filed Oct. 9, 2014, now U.S. Pat. No. 9,222,764 issued Dec. 29, 2015, which is a continuation of U.S. application Ser. No. 14/460,726 filed Aug. 15, 2014, now U.S. Pat. No. 8,941,392 issued Jan. 27, 2015, which claims the benefit of U.S. Provisional Application No. 62/003,030, filed May 27, 2014, and U.S. Provisional Application No. 61/867,047, filed Aug. 17, 2013, the entire contents of all are incorporated herein by reference.

BACKGROUND

Sensors for measuring the strain of an object are ubiquitous in the field of engineering. One type of known sensor is a capacitive strain sensor consisting of a non-conducting, compliant dielectric layer sandwiched between two compliant conducting layers (also referred to herein as "compliant electrodes"). This arrangement forms a capacitor whose capacitance depends in part on the distance between the conductive layers and the change in surface area of the compliant conducting layers. The strain and/or compression of the dielectric layer changes the capacitance of the sensor, which can be detected by a sensing system. When a beam element is bent, a tensile strain is induced on the outside of the curved beam element and a compressive strain is induced on the inside of the curved beam element. If one or more compliant capacitive strain sensors are embedded within the beam element such that they are displaced from the center axis of the beam element, the strain induced by bending results in a change in capacitance that can be detected along the length of the beam element. This change in capacitance is proportional to the curvature of the bent beam element. In turn, this curvature is proportional to the angular displacement between two vectors defined by the ends of the beam element.

BRIEF DESCRIPTION OF THE DRAWINGS

The present disclosure is illustrated by way of example, and not by way of limitation, in the figures of the accompanying drawings.

FIG. 10A is a simplified partial perspective view of an angular displacement sensor, depicting the angular displacement sensor including a set of helical or spiral compliant capacitors for sensing twisting or torque movement of the angular displacement sensor, according to another embodiment of the present disclosure.

FIG. 10B is a side view of the sensor system coupled over a shoulder joint, according to another embodiment of the present disclosure.

DETAILED DESCRIPTION

Figure 1A:
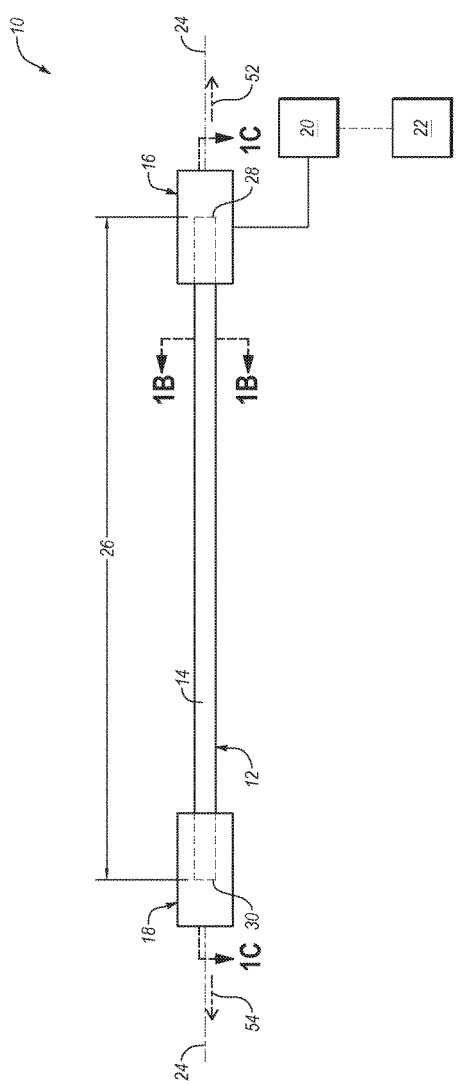
FIG. 1A is a side view of a schematic portion of a sensor system, according to an embodiment of the present disclosure.

Described herein are various embodiments of sensor systems for sensing position and movement of a joint with one, two or three rotational degrees of freedom, where each rotational degree of freedom can be described by an angular displacement occurring with a plane that is orthogonal to the planes which define the other two rotational degrees of freedom. Also, described herein are methods of operating these sensors systems to sense position and movement of a joint with one, two or three rotational degrees of freedom. Compliant capacitive strain sensors have been described which can sense strain. A number of these conventional compliant capacitive strain sensors are limited in the magnitude of strain they can be subjected to without incurring temporary or permanent damage. Temporary or permanent damage may cause a substantial increase in the resistance of the compliant electrodes of the compliant capacitive strain sensor or even a complete loss of conductivity of these conventional compliant electrodes. Even if conductivity is maintained, the resistance of conventional compliant electrodes may increase to the point that the time response of the compliant capacitive strain sensor is damaged. There are conventional compliant capacitive strain sensors that can perform measurements of bending movements, but these strain sensors have restraining elements to limit bending to prevent damage resulting from over straining. Also, these strain sensors themselves are configured to measure bending movement in one plane only. As such, the structural properties of such sensors may provide for limited bending and flexibility and, therefore, may be limited in their potential uses. The aforementioned conventional compliant capacitive strain sensors for sensing bending movements may be limited in their ability to measure bending in a single plane. Bending in a second orthogonal plane and/or torsion in a third orthogonal plane, may further compound conventional compliant capacitive strain sensors ability to quantify joints with more than one degree of freedom.

Embodiments of the present disclosure address the deficiencies described above and possibly other deficiencies of conventional sensor systems by providing an angular displacement sensor that can measure unrestricted bending movement on one or more orthogonal planes and without restraining members which restrict flexibility. The angular displacement sensor may be a flexible elongated structure or a general bending structure that has embedded strain sensing elements that could take any form. The angular displacement sensor as described herein may include a compliant strain sensing element, such as a compliant capacitor, within an elongated structure of compliant material. The elongated structure extends between a first end and a second end. The compliant material is flexible and bendable from a linear, non-bent position to multiple bendable positions. The compliant capacitor, for example, includes 1) a first conductive layer embedded within the compliant material and extending from the first end to the second end along a longitudinal length of the elongated structure to form a first electrode of the first compliant capacitor within the compliant material, 2) a second conductive layer embedded within the compliant material and extending from the first end to the second end along the longitudinal length to form a second electrode of the first compliant capacitor within the compliant material, and 3) an elastomer dielectric layer extending between the first conductive layer and the second conductive layer. Alternatively, the compliant strain sensing element may be resistive in nature, capacitive in nature, or inductive in nature. Regardless of the nature of the compliant strain sensing element, an electrical property of the compliant strain sensing element changes in proportion to an applied strain on the elongated structure as described herein in detail.

Referring to FIG. 1A, a sensor system 10 for sensing angular displacement between two vectors defined by rigid members is provided. The sensor system 10 may include an angular displacement sensor 12 with a highly bendable and flexible elongated structure 14. The angular displacement sensor 12 may be disposed within the structure 14 along a first axis extending between a first end and a second end of the structure 14.

In some embodiments, the sensor system 10 may include an angular displacement sensor 12 with a highly bendable and flexible elongated structure 14 having a first rigid member 16 and a second rigid member 18 fixed to opposing ends of the angular displacement sensor 12. The sensor system 10 may also include an interface device 20 that may be coupled to one of the rigid members. The interface device 20 may be secured to a user or object (not shown) and include various electronic components, such as a microcontroller and memory, for receiving data relative to an angular displacement, discussed in further detail herein. Further, the interface device 20 may be operatively coupled to a remote device 22 for a user to view and analyze the data received from the interface device 20.

As set forth, the angular displacement sensor 12 may be an elongated structure 14 that defines an axis 24 along a longitudinal length 26 thereof and extends between a first end 28 and a second end 30 of the angular displacement sensor 12. The first end 28 of the elongated structure 14 may be coupled to the first rigid member 16. Likewise, the second end 30 of the elongated structure 14 may be coupled to the second rigid member 18. In one embodiment, the angular displacement sensor 12 may transmit signals generated from the strain induced by bending along the elongated structure 14 utilizing one or more compliant capacitors extending along the length of the angular displacement sensor 12.

In one embodiment, the sensor system 10 may include a first compliant strain sensing element embedded within a compliant material and extending from the first end 28 to the second end 30 along a longitudinal length of the elongated structure 14. The first compliant strain sensing element may include a second compliant material that is flexible and bendable. In some embodiments, an electrical property of the first compliant strain sensing element changes in proportion to an applied strain on the elongated structure 14. The first compliant strain sensing element may be resistive in nature, where resistance of the second compliant material changes in proportion to the applied strain on the elongated structure 14. The first compliant strain sensing element may be inductive in nature, where an inductance of the first compliant strain sensing element changes in proportion to an applied strain.

In another embodiment, the angular displacement sensor 12 may utilize similar principles employing compliant inductive or resistive strain sensing elements. Further, for example, the angular displacement sensor 12 may be made of an elastomer based material with various electrode layers, dielectric layers, and other components set forth herein that enable the angular displacement sensor 12 to hold the structural characteristics of being highly flexible and bendable without breaking the electrical circuit along the length 26 of the angular displacement sensor 12.

With reference to FIGS. 1A (a side view) and 1B (an axial view of a cross section of angular displacement sensor 12), the various layers and components of the angular displacement sensor 12 will now be described, according to one embodiment. The angular displacement sensor 12 may include three primary portions: a first compliant capacitor 32 and a second compliant capacitor 34 with a base elastomer layer 36 extending therebetween, each of which extend along the longitudinal length 26 of the angular displacement sensor 12 in layers or portions. In some embodiments, the angular displacement sensor 12 includes one compliant capacitor, which may be either the first compliant capacitor 32 or the second compliant capacitor 34. Each of the first and second compliant capacitors 32, 34 includes an outer electrode 38 and an inner electrode 40 with an elastomer dielectric 42 therebetween. Each of such outer and inner electrodes 38, 40 with the elastomer dielectric 42 therebetween also extend as a layer along the longitudinal length 26 that each define a similar width 44, the width 44 defined as being transverse to the length 26 and within the same plane as the dimension of the length 26 of the elongated structure 14. The outer and inner electrodes 38, 40 may also define a thickness or depth (the dimension extending orthogonal relative to the width 44 and length 26 dimensions) such that the outer and inner electrodes 38, 40 of each of the first and second compliant capacitors 32, 34 may include a similar thickness or depth in the range of about 10-500 microns. The elastomer dielectric 42 disposed between the outer and inner electrodes 38, 40 may define a thickness or depth of about 10 to 200 microns. In addition, the base elastomer layer 36 positioned between the first and second compliant capacitors 32, 34 may include a depth in the range of about 0.5-5 mm. Such primary layers of the angular displacement sensor 12 may also include an outer layer 46 or portion (or coating) that may include a thickness of about 0.5-3 mm that is non-conductive and an elastomeric based material.

The base elastomer layer 36 or middle portion of the angular displacement sensor 12 may be either a thermoset or thermoplastic elastomer. Further, the base elastomer layer 36 is a dielectric material and non-conductive. The base elastomer layer 36 may include structural characteristics of high elongation at failure greater than 100% and preferably greater than 500%, a low durometer preferably at a 60 Shore A scale, but may be anywhere in the range of 1-90 on the Shore A scale. In addition, the base elastomer layer 36 may include a low compression set of 1-30%. In one embodiment, a thermoset elastomer may include tin or platinum cured silicone elastomers and/or polyurethane elastomer components or any other suitable elastomer material. In another embodiment, a thermoplastic elastomer may include components of styrene-ethylene/butylene-styrene (SEBS), styrene-block-butadiene-block-styrene (SBS), and/or polyurethanes or any other suitable thermoplastic elastomer.

The first and second compliant capacitors 32, 34 of the angular displacement sensor 12 may be a partially conductive material (and an elastomer based material) so as to store a charge and be formed over opposite sides of the base elastomer 36. As previously set forth, each of the first and second compliant capacitors 32, 34 may include the outer and inner electrodes 38, 40 with the elastomer dielectric 42 therebetween. The elastomer dielectric 42 between the outer and inner electrodes 38, 40 may be non-conductive and formed of a similar material as the base elastomer 36. The outer and inner electrodes 38, 40 may be formed along a length 26 of the elongated structure 14 as layers of an elastomer based material with a conductive filler. In one embodiment, the conductive filler may include powdered or flake metals, such as silver flake, carbon black and fibrous materials such as carbon nanofibers, carbon nanotubes, silver nanostrands or any other suitable conductive filler particles. It is preferable to use the minimum amount of conductive filler particles as possible, as excess filler concentrations alters the elastic behavior of the elastomer. Excessive conductive filler particles may limit the ability of the angular displacement sensor 12 to effectively bend and result in an electrical circuit break through bending the angular displacement sensor 12. The embodiments described herein may facilitate maximum bending by limiting the conductive filler particles in the elongated structure 14. As such, to minimize the conductive filler in the electrode layers to, thereby, minimize breaking the electrical circuit in the outer and inner electrodes 38, 40, the elongated structure 14 may also include a conductive wire member.

Figure 1B:
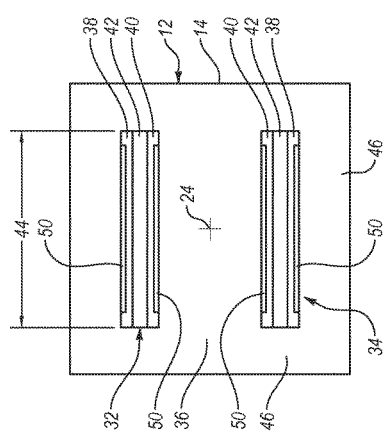
FIG. 1B is a cross-sectional view taken along section line 1B of FIG. 1A, depicting components of an angular displacement sensor of the sensor system, according to another embodiment of the present disclosure.
Figure 1C:
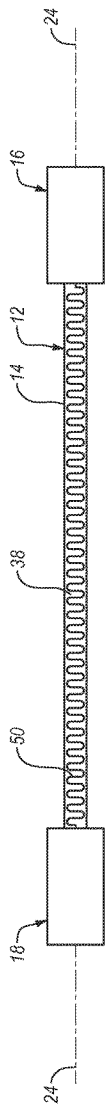
FIG. 1C is a cross-sectional view taken along section line 1C of FIG. 1A, depicting a spring electrode of the sensor system, according to another embodiment of the present disclosure.

Now with reference to FIGS. 1B and 1C, the conductive wire member may extend continuously through the elongated structure 14 between the first and second ends 28, 30 thereof. In one embodiment, the wire member may include a wave configuration, similar to a sine wave, and be a spring-like structure, referenced as a spring electrode 50. The spring electrode 50 may be made from a conductive metal and may be formed in a shape that can easily elongate, compress, and twist about or along the axis 24 of the angular displacement sensor 12. The spring electrode 50 may be formed from a wire or laser cut from flat sheets, or formed via etching photolithography techniques. The material of the spring electrode 50 may be any conductor, including stainless steel, copper, super-elastic materials, such as Nitinol, or any other suitable conductive material. In one embodiment, the spring electrode 50 may extend in a flat configuration or be planer with the wave configuration, as depicted. In another embodiment, the spring electrode 50 may be helical or some other three-dimensional shape such that the helical configuration extends through the conductive layers. In another embodiment, the conductive layers may extend through the elongated structure 14 in a helical configuration with the spring electrode 50 disposed along the conductive layers.

The spring electrode 50 may be embedded through each of the layers of the outer and inner electrodes 38, 40. In another embodiment, the spring electrode 50 may be positioned over a surface of each of the outer and inner electrodes 38, 40. Each of the outer and inner electrodes 38, 40 may include its own spring electrode 50, separate and discrete from each other. The spring electrodes 50 are intended to make electrical contact within the compliant electrode layers, and as such, may be just touching the electrode material or either partially or fully embedded in the compliant electrode layers. Further, the spring electrode 50 may be positioned over or in each of the outer and inner electrodes 38, 40 by laying the spring electrode 50 onto the surface of the outer and inner electrodes 38, 40 and pressing the spring electrode 50 into the surface, which may embed at least a portion of the spring electrode 50 into the electrode layers. With the spring electrode 50 at least partially embedded into each of the outer and inner electrodes 38, 40, such spring electrode 50 minimizes potential breaks in the electrical circuit in the conductive elastomer of the outer and inner electrodes 38, 40. Such spring electrode 50 may maintain a proper electrical circuit and connection to minimize potential circuit breaks in instances, for example, where the angular displacement sensor 12 is moved to a maximum bent position, the angular displacement sensor 12 becomes fatigued through reiterative minimal or maximum bending, and/or unforeseen instances where the angular displacement sensor is misused or mishandled. Further, the spring electrode 50 places little to no resistance to the bendability of the angular displacement sensor 12. Furthermore, the spring electrode 50 facilitates minimizing the conductive filler particles of the outer and inner electrodes, thus, maximizing the bendability of the angular displacement sensor 12. In this embodiment, as previously set forth, there may be two pairs of outer and inner electrodes 38, 40 and, thus, there would be four spring electrodes 50 extending through the angular displacement sensor 12, one for each electrode layer. Of course, there may be instances where there may be more spring electrodes or conductive wire members per electrode or additional electrodes each containing at least one conductive wire member. In addition, the spring electrodes 50 facilitate coupling the outer and inner electrodes 38, 40 to wire leads (not shown) extending in one or both of the first and second rigid members 16, 18 for transferring measurement data from the first and second compliant capacitors 32, 34. Such wire leads transfer measurement data to a differential capacitance measurement circuit 112 (FIG. 7), discussed in further detail herein.

Figure 2A:
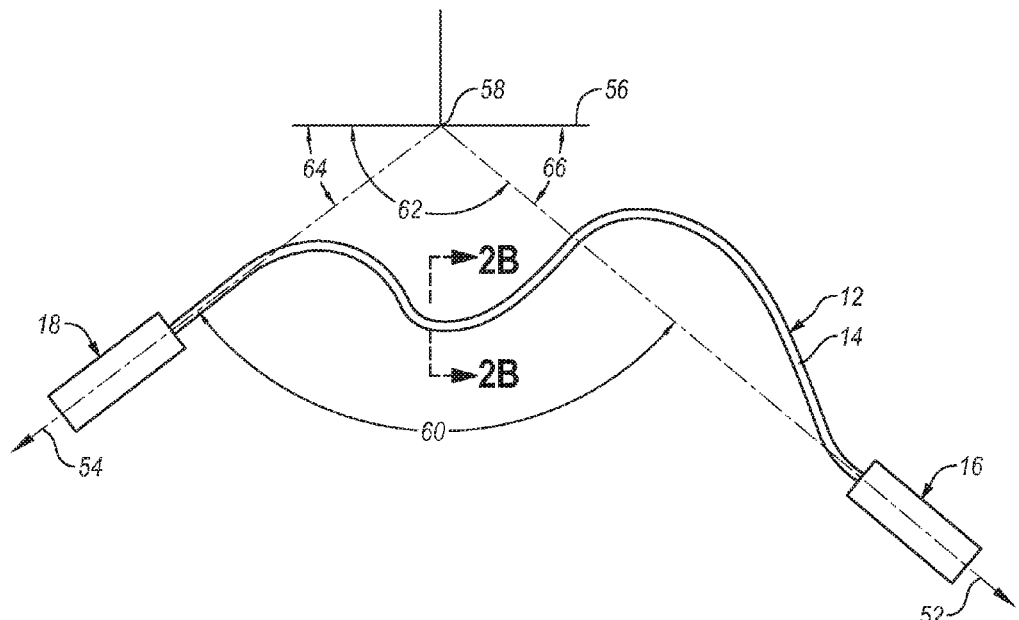
FIG. 2A is a side view of a sensor system, depicting an angular displacement of the angular displacement sensor, according to one embodiment of the present disclosure.

With respect to FIGS. 1A and 2A, the sensor system 10 is depicted in a linear non-bended, first position and a bended, second position, respectively. As previously set forth, the sensor system 10 may include the angular displacement sensor 12 or middle region that is an elastomer based material formed into an elongated structure 14 that is highly flexible and/or bendable. The sensor system 10 may include an elongated structure 14 extending between a first end 28 and a second end 30. The elongated structure may be a compliant material that is flexible and bendable from a linear, non-bent position to multiple bendable positions. The first and second ends 28, 30 of the angular displacement sensor 12 are embedded within or attached to the respective first and second rigid members 16, 18 that may also be somewhat elongated and preferably symmetrically formed around the first and second ends 28, 30 of the angular displacement sensor 12. The rigid members 16, 18 may fully or partially embed the angular displacement sensor ends 28, 30. Alternatively, the rigid members 16, 18 may be embedded within the angular displacement sensor ends 28, 30 either partially or fully. Furthermore, the rigid members 16, 18 may take the form of adhesives, screws, welds, or other form of attachments between the sensor ends 28, 30 and the substrate to which the angular displacement sensor 12 is attached. The substrate to which the angular displacement sensor 12 is attached may include plastic, metal, ceramics, fabric, elastomers and the like. The first and second rigid members 16, 18 may define a first vector 52 and a second vector 54, respectively. In the linear non-bended position, the first and second vectors 52, 54 may be substantially co-axial with the axis 24 of the elongated structure 14 or co-axial with the angular displacement sensor portion itself.

In the non-linear bended position, the first and second rigid members 16, 18 may become displaced such that the elongated structure 14 is non-linear or moved to a bent position. In this bent position, the first and second vectors 52, 54 defined by the respective first and second rigid members 16, 18 define an angle or, otherwise referenced herein as, an angular displacement 60 between the first and second rigid members 16, 18. In one embodiment, the angular displacement 60 may be determined from, for example, a horizontal line 56, relative or parallel to the axis 24 of the angular displacement sensor 12 in the linear position, taken from an intersection 58 of the first and second vectors 52, 54. As such, the angular displacement 60 may be equal to a first vector angle 62 minus a second vector angle 64, in which the first vector angle 62 may be defined between the horizontal line 56 and the first vector 52 and the second vector angle 64 may be defined between the horizontal line 56 and the second vector 54. Other angles, such as an acute angle 66 defined between the second vector 54 and the horizontal line 56, may also be of interest and may have need to be analyzed, which may readily be calculated as a parameter, as known to one of ordinary skill in the art. In this manner, the sensor system 10 may provide measurement data to calculate the angular displacement 60 between the first and second vectors 52, 54 defined by the first and second rigid members 16, 18. The angular displacement sensor 12 also may provide measurement data as to the change in the angular displacement 60 over time as well a rate of change of the angular displacement 60 between the first and second vectors 52, 54 defined by the first and second rigid members 16, 18.

The angular displacement 60 is measured, as well as each of the above noted angles, with a differential measurement based on the capacitance output of the first and second compliant capacitors along the length 26 of the elongated structure 14 or angular displacement sensor 12. The angular displacement 60 is detected by measuring the capacitance between the inner and outer electrodes of each of the first and second compliant capacitors 32, 34. The differential measurement of the first and second compliant capacitors increases the sensitivity and reduces common mode noise. In some embodiments, the first and second compliant capacitors 32, 34 are spaced in a parallel manner such that a sensitivity of the angular displacement is increased. The first and second compliant capacitors are offset from a center axis of the elongated structure and are reflected about the center axis. In some embodiments where the angular displacement sensor 12 includes a single compliant capacitor, the angular displacement 60 is detected by measuring the capacitance between the inner and outer electrodes of the single compliant capacitor.

Upon the first and second rigid members 16, 18 being in a co-axial position, as shown in FIG. 1A, the measurement data transmitted from the angular displacement sensor 12 will indicate substantially no angular displacement. The same is true upon the first and second rigid members 16, 18 being parallel with each other since any positive/negative capacitance generated due to bending in the angular displacement sensor 12 will cancel each other out. On the other hand, upon the rigid members being moved to an orientation that is non-coaxial or non-parallel, such as that shown in FIG. 2A, the capacitance measurements provided by the angular displacement sensor 12 may provide an angular displacement 60 relative to the orientation between the first and second vectors 52, 54 defined respectively by the first and second rigid members 16, 18.

Figure 2B:
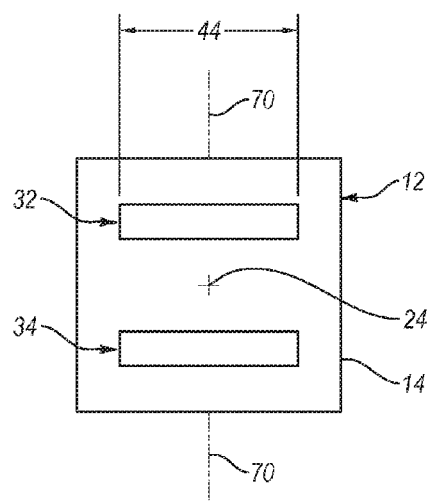
FIG. 2B is a cross-sectional view of the angular displacement sensor taken along section line 2B of FIG. 2A, depicting a plane extending along an axis of the angular displacement sensor and orthogonal to a width of compliant capacitors of the angular displacement sensor, according to another embodiment of the present disclosure.

With respect to FIGS. 2A and 2B, in one embodiment, the angular displacement 60 is calculated along and within a first plane 70 or a projection or component of the first plane 70 relative to the first and second rigid members 16, 18 and the angular displacement sensor 12. In other words, due to the flexibility of the elongated structure 14, the first and second rigid members 16, 18 and/or elongated structure 14 may extend out of the first plane 70 and, thus, the angular displacement 60 that may be measured may be a projection or components of the first plane 70 relative to the actual position of the angular displacement sensor 12. The first plane 70 may be defined as a plane corresponding with and/or extending along the axis 24 of the angular displacement sensor 12 and extending substantially orthogonal to the width 44 of the first and second compliant capacitors 32, 34 of the angular displacement sensor 12. The width 44 of the compliant strain sensor 44 may be defined as the dimension orthogonal to the longitudinal length 26 (see FIGS. 1A and 1B), the width 44 and length 26 dimensions extending within the same plane. In some embodiments, the width of the compliant strain sensor 44 may be defined as a distance between the two sides of the compliant strain sensor 44 that lie within a plane perpendicular to an axis of the elongated structure and perpendicular to the plane in which angular displacement is being measured such that this axis corresponds to the angular displacement sensor 12.

Furthermore, the angular displacement 60 may be defined solely by the angle between the first and second vectors 52, 54 defined by the first and second rigid members 16, 18. That is, the sensor system 10 may only provide measurement data for the angular displacement 60 relative to the first and second vectors 52, 54 and is insensitive to the path of the angular displacement sensor 12, including any wrinkles, kinks, out of plane bending, etc. of the angular displacement sensor 12 itself. For example, in FIG. 2A, the angular displacement sensor 12 is bent similar to an "M" configuration. However, as set forth, the differential measurement of the first and second compliant capacitors (FIG. 2B) is limited to the angular displacement 60 of the first and second vectors 52, 54 defined by the first and second rigid members 16, 18.

Figure 3:
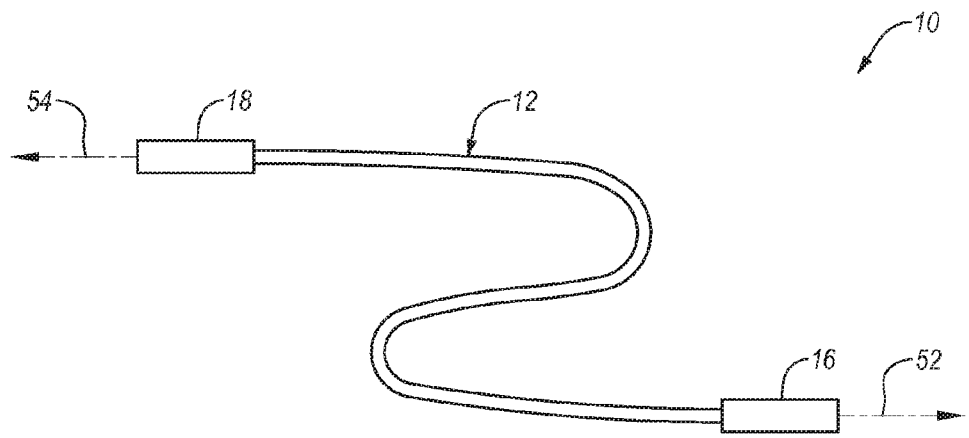
FIG. 3 is a side view of the sensor system, depicting rigid ends of the angular displacement sensor extending substantially parallel relative to each other, according to another embodiment of the present disclosure.

Further, for example, FIG. 3 depicts the angular displacement sensor 12 of the sensor system 10 being bent in several locations similar to an "S" configuration. However, in this "S" configuration, the first and second vectors 52, 54 defined by the respective first and second rigid members 16, 18 are substantially parallel to each other and, thus, there is no angular displacement between the first and second vectors 52, 54. In this manner, the positive and negative capacitance measurements of the angular displacement sensor 12 in the differential measurement would cancel each other out to provide measurement data with no angular displacement between the first and second vectors 52, 54.

Figure 4:
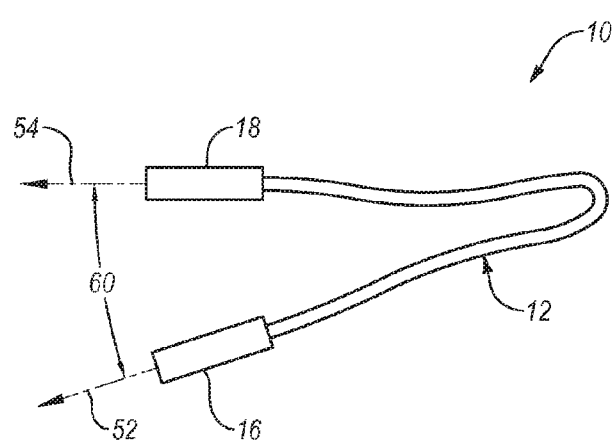
FIG. 4 is a side view of the sensor system, depicting the flexibility of the angular displacement sensor, according to another embodiment of the present disclosure.

In another example, FIG. 4 depicts the high flexibility of the angular displacement sensor 12 such that the angular displacement sensor 12 may bend over itself as it is a highly bendable elastomer based sensor (without restraint), as previously set forth. The non-restrained flexible angular displacement sensor 12 of the present embodiment is advantageous as such an angular displacement sensor 12 may be employed over a variety of anatomical joints or for other useful purposes with limited potential of breaking its electrical circuit therein. It is noted that a non-restrained flexible angular displacement sensor 12 may be defined as not having one or more members associated with the angular displacement sensor 12 to positively limit its flexibility or bendability, but rather, the non-restrained flexible angular displacement sensor 12 may only be restrained by the elastomer based materials of the angular displacement sensor 12 itself. As such, the non-restrained angular displacement sensor 12 may be employed without breaking the electrical circuit along the first and second compliant capacitors in the angular displacement sensor 12 due to the spring electrodes 50 (FIGS. 1B and 1C) positioned within each of the outer and inner electrodes 38, 40 of the compliant capacitors 32, 34, as described herein, or by utilizing a conductive elastomeric electrode material (such as an elastomer with certain fibrous conductive filler materials, such as carbon nanotubes) that maintains conductivity at high strains. Further, as depicted in FIG. 4, the sensor system 10 calculates the angular displacement 60 between the first and second vectors 52, 54 defined by the respective first and second rigid members 16, 18, regardless and accounting for the minimized radius or bend in the angular displacement sensor 12.

Figure 5A:
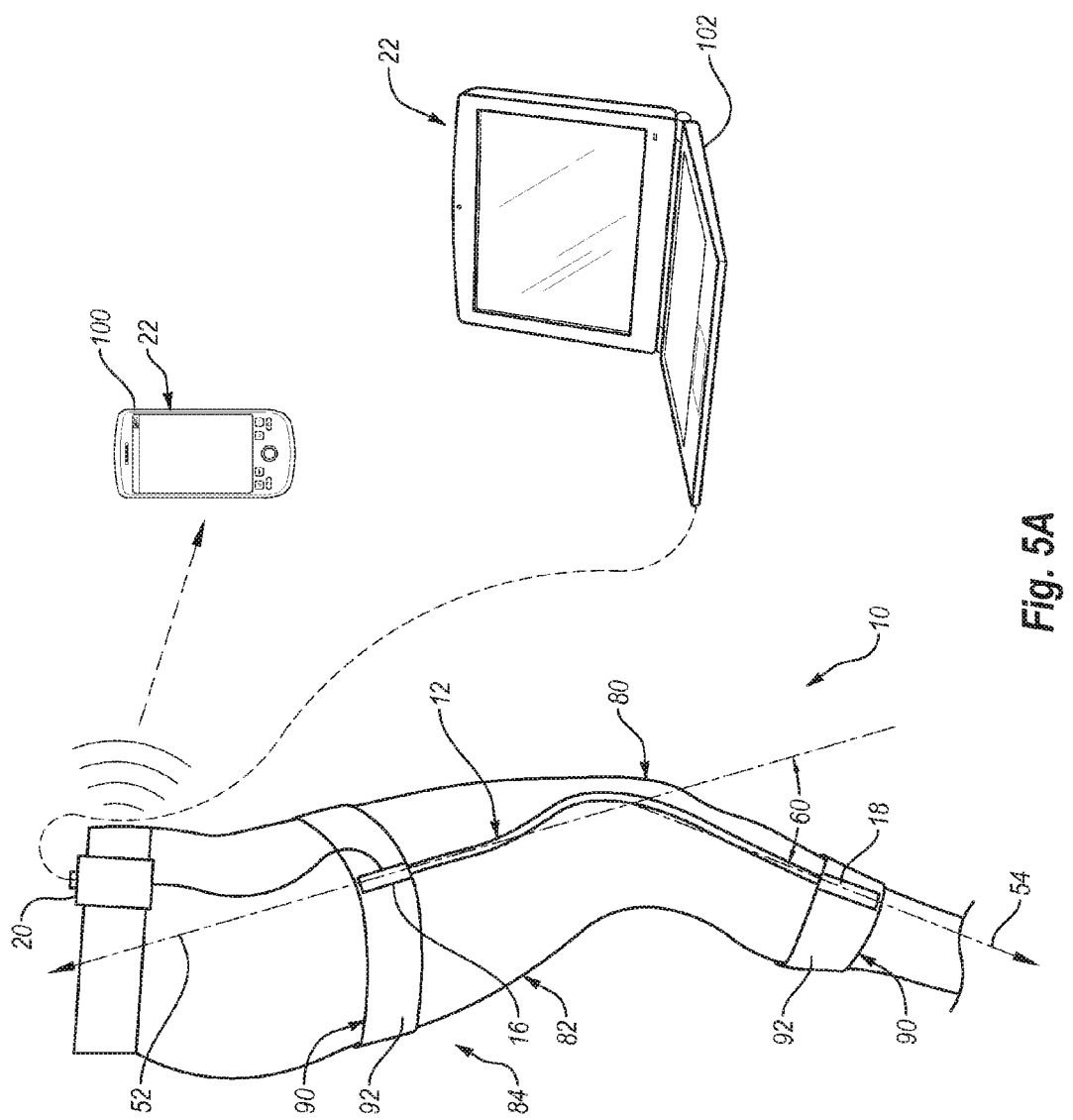
FIG. 5A is a side view of the sensor system coupled over an anatomical joint of a leg, depicting rigid ends of the sensor system having registration members for attaching to the leg, according to another embodiment of the present disclosure.

Now with reference to FIG. 5A, the sensor system 10 is depicted in use with the angular displacement sensor 12 extending over an anatomical joint 80, such as a knee joint, with the first and second rigid members 16, 18 coupled to a leg 82 of a person or user 84. In one embodiment, the first and second rigid members 16, 18 may each include a registration member 90 coupled, secured, or attached thereto. The registration member 90 may include one or more straps 92 to form a strap arrangement. Such straps 92 may be adhesively attached or sewn to the first and second rigid members 16, 18 and may include one or more straps 92, including hook and loop fasteners such as in the Velcro® straps, to readily attach and remove the one or more straps 92 from one's leg 82, for example. In this manner, the registration member 90 may wrap around, for example, a person's leg 82 under or over clothing to fixedly orient and position the first and second rigid members 16, 18 proximal and distal the anatomical joint 80 of the user 84.

Figure 6:
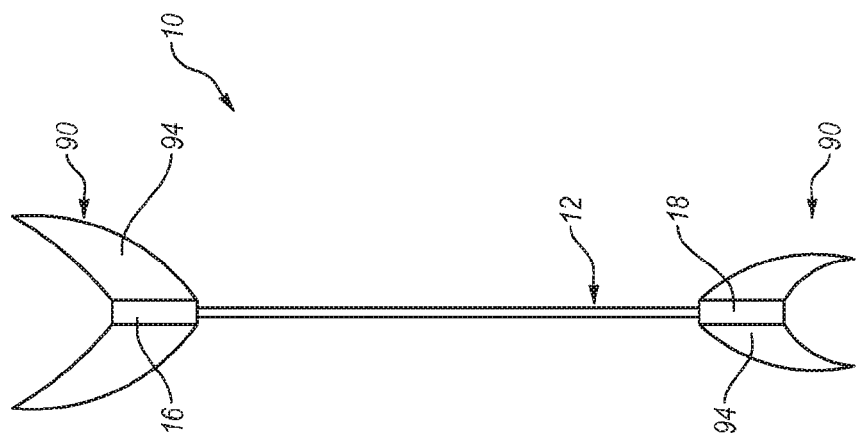
FIG. 6 is a side view of the sensor system, depicting another embodiment of the registration members extending from the rigid members of the angular displacement sensor, according to the present disclosure.

In another embodiment, the registration member 90 associated with the sensor system 10 and angular displacement sensor 12 may include flange portions 94 in a fin-like structure, as depicted in FIG. 6. Alternatively, the flange portions 94 may be in a rectangular, ellipsoidal or other geometrically shaped structure. In this embodiment, the first and second rigid members 16, 18 may be disposed in a pocket, slot or sleeve of one's clothing (not shown) that is sized and configured to receive the flange portions 94 of the registration member 90 such that the registration member is integrated with the clothing itself. Of course, the flange portions 94 may include other configurations that include a surface area that will maintain the rigid members in a fixed orientation adjacent the anatomy that may be integrated into clothing. In another embodiment, the first and second rigid members 16, 18 may simply be integrated within clothing, without flange portions, in a manner that will hold the first and second rigid members 16, 18 in a substantially fixed orientation within the clothing. In this manner, the registration member 90 may be sized and configured with any suitable structure for being fixedly positioned to the anatomy of the person or user. With respect to FIGS. 5A and 6, in another embodiment, the registration member 90 may replace the first and second rigid members 16, 18 such that the registration member 90 facilitates positioning the first and second ends 28, 30 (FIG. 1A) of the angular displacement sensor 12 in a substantially fixed position against the anatomy of the user 84 to act or perform as a rigid member.

Referring back to FIG. 5A, in one embodiment, the first rigid member 16 may be positioned proximal and above the anatomical joint 80 and the second rigid member 18 may be positioned distal and below the anatomical joint 80. Such first and second rigid members 16, 18 may be positioned so that the angular displacement sensor 12 or middle portion of the sensor system 10 may extend over or adjacently along the side of the anatomical joint 80. The interface device 20 may be coupled to the waist of the user 84 or simply placed in the user's pocket or the like. As the user 84, for example, performs a walking or running motion, the angular displacement sensor 12 bends along multiple bent positions between the first and second rigid ends 28, 30. Upon undergoing such motion, the interface device 20 receives, logs and saves data relative to the angular displacement 60 between the first and second vectors 52, 54. In this manner, the logged data may then be transmitted to the remote device 22 wirelessly to, for example, a mobile device 100 (e.g., smart phone) using wireless technology or transferred with, for example, a storage device via a wired connection (e.g., universal serial bus (USB) port) to a personal computer 102. Other means for transferring logged data to the remote device 22 may be employed, as known to one of ordinary skill in the art having the benefit of this disclosure. Once transferred to the remote device 22, the logged data may be put in various formats useable for analysis. In this example where the angular displacement sensor 12 is positioned over a knee joint, the user or physician may better understand the person's gait, as well as the rate of angular displacement 60 and even the change in the angular displacement 60 of the person changing from a walking motion to a running motion. In this manner, the logged data may be transferred to the remote device 22, saved, and viewable for later analysis. Further, a physician, for example, may chart the progress/decline and compare differences in the user's gait over various sessions and periods of time.

Figure 5B:
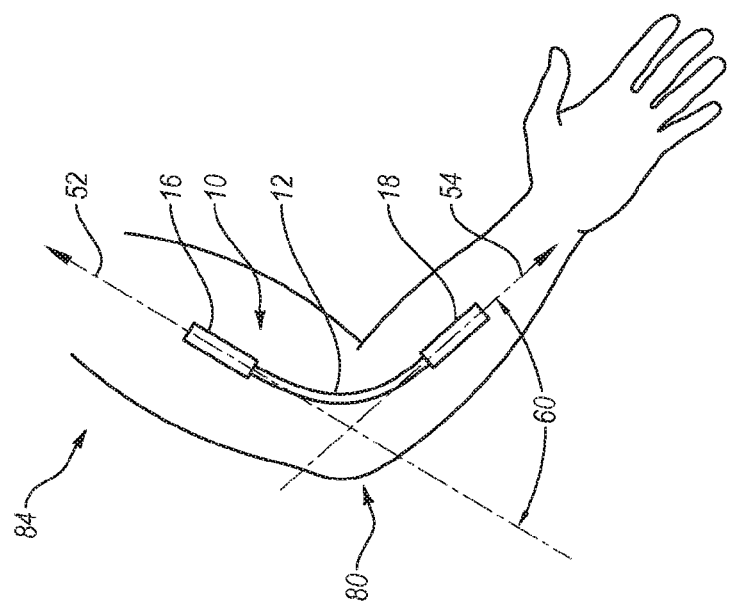
FIG. 5B is a side view of the sensor system, coupled over an anatomical joint of an arm, according to another embodiment of the present disclosure.

The sensor system 10 may be employed for similar analysis to graph and analyze other anatomical joints 80, such as an elbow joint, as depicted in FIG. 5B. The elbow joint is similar to the knee joint in that the elbow joint moves substantially within a single plane or a first plane 70 (see FIG. 2B). As such, the first rigid member 16 may be positioned proximal the elbow joint and the second rigid member 18 may be positioned distal the elbow joint with the angular displacement sensor 12 extending over or adjacent the side of the elbow joint. The sensor system 10 may undergo reiterative arm movements at the elbow joint in which the sensor system 10 measures and calculates data relative to the angular displacement 60 between the first vector 52 and the second vector 54 defined by the respective first and second rigid members 16, 18. Similar to that described relative to FIG. 5A, the data may be logged and transferred to a remote device 22 for analysis. For example, a user 84 or patient may be injured and undergoing rehabilitative physical therapy and precise measurements of the angular displacement 60 may be useful to understanding the progress or decline of the patient 84 over various sessions and periods of time.

Figure 7:
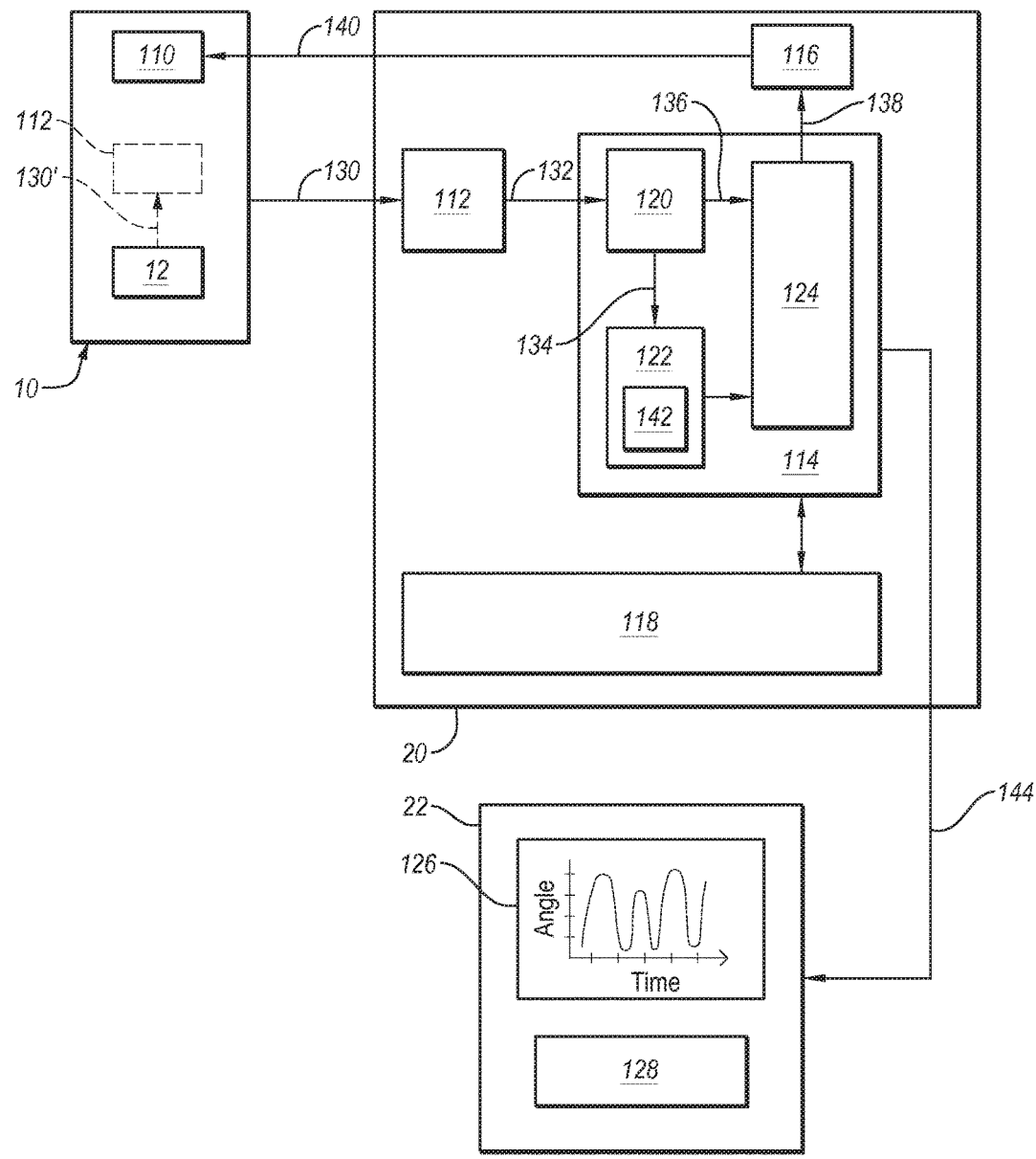
FIG. 7 is a schematic of the sensor system, according to another embodiment of the present disclosure.

With respect to FIG. 7, a schematic diagram or flow chart of various components of a system for analyzing data relative to angular displacement of the sensor system 10, according to one embodiment, is provided. In this embodiment, the primary components may include the sensor system 10, the interface device 20, and the remote device 22. The sensor system 10 may include the angular displacement sensor 12 and a biofeedback device 110. The interface device 20 may include a capacitance measurement circuit 112, a micro-controller 114, a biofeedback amplifier 116, and a user interface 118. The micro-controller 114 may include a calculation circuit 120, a memory 122, and control and analysis software 124. The remote device 22 may include a display 126 and user input 128, and may include the processors and computing devices of, for example, a smart phone or personal computer, as known in the art. In other embodiments, the micro-controller 114 may include both analog and digital circuitry to perform the functionality of the capacitance measurement circuit 112, the calculation circuit 120, and biofeedback amplifier 116.

In use, for example, upon bending movement of the angular displacement sensor 12, the capacitance measurement circuit 112 measures capacitances of the compliant capacitors 32, 34 of the angular displacement sensor 12. As illustrated in FIG. 7, the capacitance measurement circuit 112 can be housed in the interface device 20 and coupled to the angular displacement sensor 12 via wires, as indicated by arrow 130 Alternatively, the capacitance measurement circuit 112 may be housed adjacent to or with the angular displacement sensor 12 itself (as indicated with dashed arrow 130' in FIG. 7) or within, for example, one of the first and second rigid members (not shown) coupled to the angular displacement sensor 12. It should be noted that the capacitance measurement circuit 112 can measure a first capacitance between the inner electrode 40 and outer electrode 38 of one of the compliant capacitors 32, 34. The capacitance measurement circuit 112 can also measure a second capacitance between the inner electrode 40 and outer electrode 38 of the other one of the compliant capacitors 32, 34. In another embodiment, the capacitance measurement circuit 112 can measure a differential capacitance of the two compliant capacitors 32, 34. When the angular displacement sensor 12 includes the single compliant capacitor, as described herein, the capacitance measurement circuit 112 can measure a single capacitance between the inner and outer electrodes of the single compliant capacitor. The capacitance measurement circuit 112 can measure the capacitance(s) or differential capacitance in terms of voltage. The capacitance measurement circuit 112 then transmits voltage data to the micro-controller 114, such as to the calculation circuit 120, as indicated by arrow 132. The calculation circuit 120 calculates the values of the voltage data provided by the capacitance measurement circuit 112 to calculate the angular displacement 60 (see FIG. 5A) between the first and second vectors 52, 54 defined by the sensor system 10, as previously described. The calculation circuit 120 may then transmit angle data to the memory 122 (which then becomes logged data) and the control and analysis software 124, as indicated by respective arrows 134, 136. In one embodiment, parameters may be input as maximum/minimum limits for angular displacement through, for example, the user interface 118. The user interface 118 may include a display and/or a user input, such as input keys. The maximum limits (and minimum limits) may be useful for a user to know once the user has reached a particular angular displacement with the sensor system 10. As such, if the user does meet the desired parameters (or undesired as the case may be), the control and analysis software 124 may transmit a signal to the biofeedback amplifier 116, as indicated by arrow 138, which in turn may transmit a signal back to the biofeedback device 110, as indicated by arrow 140, at the sensor system 10.

The biofeedback device 110 may then produce a notification to the user that a predefined input parameter has been reached, such as the maximum angular displacement, so that the user understands in real-time the limits relative to the movement of the user's particular joint being analyzed. The notification may be at least one of a visual notification, an audible notification, and a tactile notification or some other notification to facilitate the user's understanding of the user's maximum limit. Alternatively, the notification can be any combination of visual, audible and tactile notifications. The visual notification may be in the form of a blinking (or various colored) light or the like displayed on the sensor system 10 itself or the interface device 20 and/or also may be visualized on a display of the interface device 20. The audible notification may be a ring or beep or the like that may preferably be audibly transmitted from the interface device 20, but may also be transmitted from the sensor system 10. The tactile notification may be coupled to or integrated with one of the first and second rigid members 16, 18 (FIG. 5A) of the sensor system 10 or may be integrated in the interface device 20. Such tactile notification may be in the form of a vibration or some other tactile notification, such as a compression member. In this manner, the biofeedback device 110 may notify the user in real time upon extending or contracting ones anatomical joint at a maximum angular displacement according to a predetermined input parameter. Similarly, in another embodiment, a user may input parameters of a minimum angular displacement into the interface device 20 for biofeedback notification. Further, in another embodiment, the user may input parameters for both a minimum angular displacement and a maximum angular displacement. Inputting such parameters may be useful for exercises during physical therapy and for athletes training to obtain particular movements at various anatomical joints.

Upon completing a session of rehabilitation therapy or training or the like, logged data 142 may be stored in the memory 122 or storage device of the interface device 20. Such logged data 142 may also be viewable on the interface device 20 on a display at the user interface 118. The logged data 142 may then be transferred to the remote device 22, as indicated by arrow 144. The remote device 22 may be any known computing device, such as a mobile device, smart phone, tablet, personal computer, gaming system, etc. In one embodiment, the logged data 142 may be transferred to a smart phone by, for example, wireless technology (e.g., over a wireless local area network (WLAN) such as a Bluetooth® network or Wi-Fi® network) or transferred via mini-USB ports or the like, as known to one of ordinary skill in the art. In another embodiment, the logged data 142 may be transferred to a personal computer via a port, such as a USB port with, for example, a portable memory device, such as a thumb drive. The user may then save the logged data 142 on the remote device 22 for further analysis. As previously set forth, the user may save several sessions of logged data 142 to the remote device 22 to obtain further analysis and comparison data to better understand, for example, progress or regress in the user's angular displacement of the user's anatomical joints.

Figure 8A:
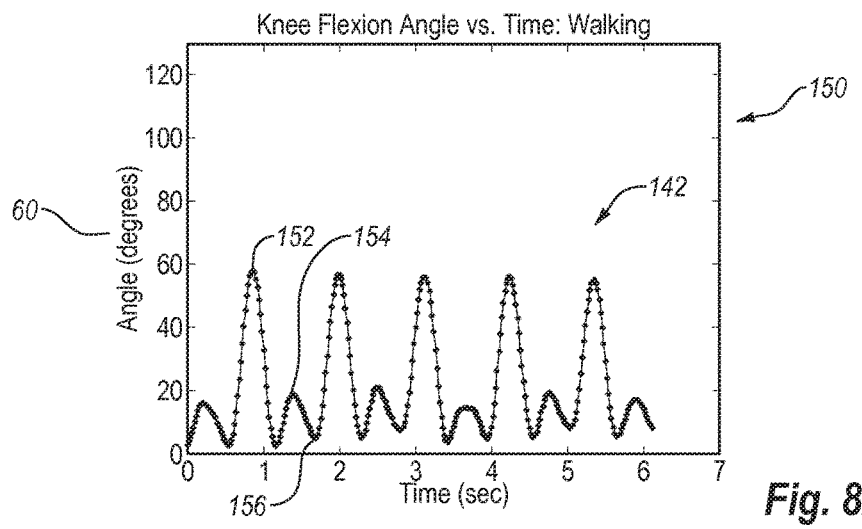
FIGS. 8A, 8B, and 8C are graph charts, depicting examples of calculated data shown as angle verses time graphs, according to another embodiment of the present disclosure.
Figure 8B:
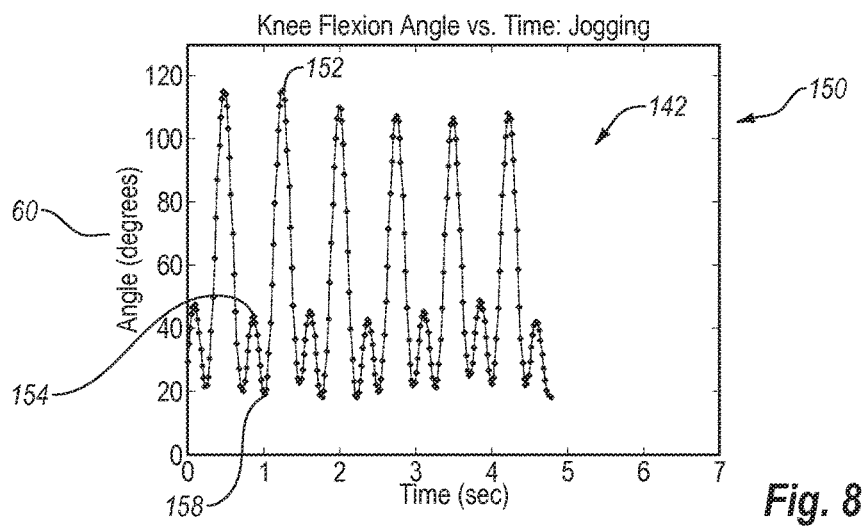
Figure 8C:
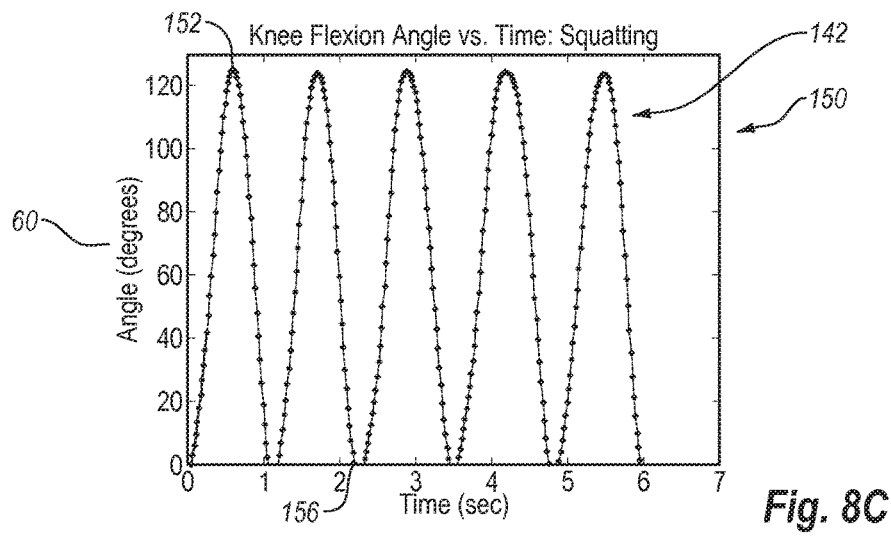

As depicted in FIGS. 8A, 8B, and 8C, one embodiment of logged data 142 provided by the sensor system coupled to a user's knee joint, similar to that depicted in FIG. 5A, is provided. For example, FIG. 8A graphs logged data 142 that a user may view on a remote device 22, such as, a personal computer, in the form of a graph 150, providing logged data 142 of the angular displacement 60 at the knee joint verses time of the user performing a walking motion. As depicted, the logged data 142 provides the user's gait with an angular displacement 60, depicting a maximum angle 152 of about 60 degrees with a minimal bump angle 154 of about 15-20 degrees between each maximum angle 152. Further, between each maximum angle 152 and minimal bump angle 154, the user's leg extends almost vertical or at about a zero angular displacement 156. Such logged data 142 also provides detail relative to the rate of the user's walking or gait.

In another example, FIG. 8B provides logged data 142 in graph format of a user jogging, providing detail of the angular displacement verses time. The graph of the user jogging is similar to the user walking, except the maximum angle 152 ranges between 110 and 115 degrees with the minimal bump angle 154 of about 40 degrees. Further, the angular displacement 60 of the knee joint does not appear to ever register at a zero angular displacement or extend linearly, but rather, always maintains a minimal angular displacement 158 of at least 20 degrees. FIG. 8C provides logged data 142 in graph format of a user performing a squatting motion, showing detail of the angular displacement 60 of the knee while squatting verses time. In this embodiment, the angular displacement 60 moves between a minimal angular displacement 156 of about zero degrees and the maximum angle 152 of about 120 degrees.

As described above, such logged data 142 may be useful for physical therapists for recording improvement in persons recovering from an injury. Similarly, physicians may desire to record and analyze the decline of a patient with an illness. Further, athletes may be able to utilize such logged data in order to analyze their gait and to understand where improvements can be made and compare past logged data to view and analyze such improvements. Furthermore, with respect to FIGS. 5A and 7, as previously discussed herein, the sensor system 10 may include the biofeedback device 110. The biofeedback device 110 may be integrated with one of the rigid ends or in the interface device 20. The biofeedback device 110 may be sized and configured to alert or notify the user of a maximum or minimum angular displacement that the user 84 inputs as a parameter in which the joint should or should not extend (or contract or twist, see FIG. 10A). In one embodiment, the biofeedback device 110 may exhibit a flashing light, provide a tactile signal (e.g., vibration), and/or provide an audible sound, so that the user 84 is notified of a predetermined angular displacement 60 or movement of one's joint.

For example, during rehabilitative physical therapy, the sensor system 10 may be programmed with a parameter to activate the biofeedback device 110 upon moving one's leg at the given predetermined angle translated as the angular displacement 60 between the first and second vectors 52, 54 defined by the relative first and second rigid members 16, 18. The user 84 may attach the sensor system 10 to, for example, one's leg to extend along the anatomical joint 80, such as the knee joint. The user 84 may undergo physical therapy by reiterating certain movements of the knee joint such that the predetermined angle is set so that the biofeedback device 110 notifies the user once the correct movement or angle has been obtained or met. Likewise, the sensor system 10 can be programmed to notify the user 84 prior to exceeding an angular displacement corresponding with the anatomical joint 80 that the user is making to minimize joint movement that may be harmful to the user. In this manner, the sensor system 10 can be utilized for physical therapy or the like. Also, as previously set forth, the sensor system 10 may be employed for other anatomical joints of the anatomy, such as the ankle joint, the shoulder joint, and/or the hip joint. As will be apparent to one of ordinary skill in the art, some joints in the body allow bending movement and/or rotational movement outside of a single plane. As such, the sensor system 10 may be sized and configured with additional compliant capacitors to account for bending of the sensor in additional planes or rotational movement.

Figure 9A:
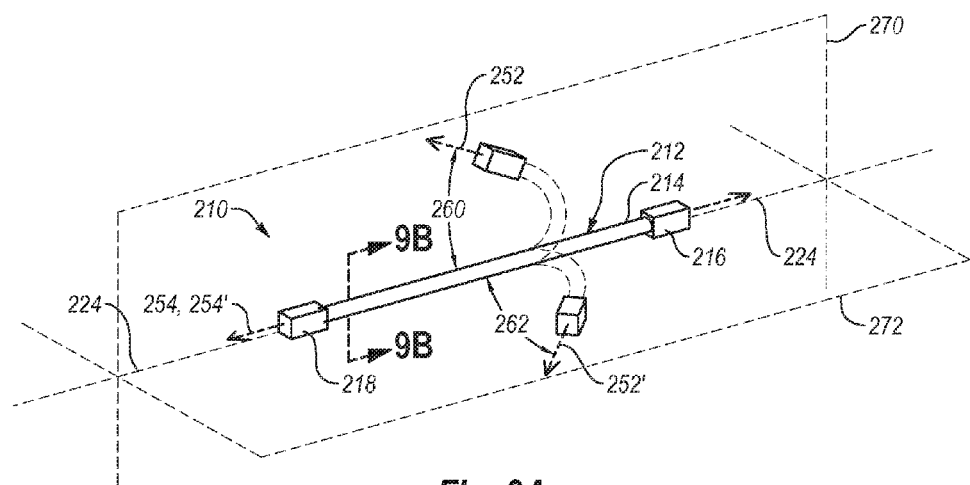
FIG. 9A is a perspective view of a sensor system, depicting the sensor system sensing angular displacement in a first plane and a second plane, according to another embodiment of the present disclosure.
Figure 9B:
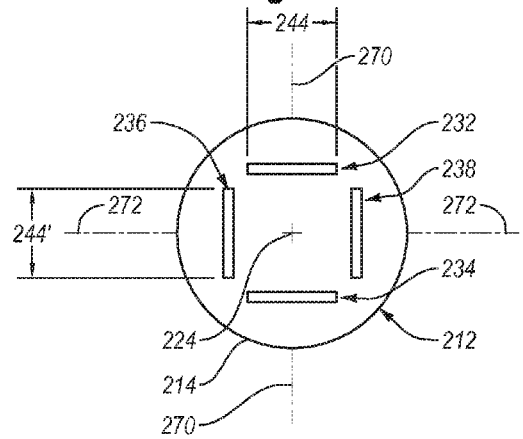
FIG. 9B is a cross-sectional view of the angular displacement sensor taken along section line 9B of FIG. 9A, depicting the angular displacement sensor including first and second sets of compliant capacitors for sensing angular displacement in a first plane and a second plane, according to another embodiment of the present disclosure.

For example, with respect to FIGS. 9A and 9B, another embodiment of a sensor system 210 is provided. In this embodiment, the sensor system 210 may include an angular displacement sensor 212 with an elongated structure 214 with first and second rigid members 216, 218 at opposing ends of the elongated structure 214. The sensor system 210 of this embodiment is similar to the embodiments described above, except in this embodiment, the angular displacement sensor 212 may include an additional pair of compliant capacitors, resulting in a total of four compliant capacitors 232, 234, 236, 238, described in more detail below. The angular displacement sensor 212 may also include a round periphery, as shown in the cross-sectional view of FIG. 9B, however such may also include a square, rectangular, ellipsoidal, or round periphery, or any other regular or non-regular shape. The angular displacement sensor 212 includes first and second compliant capacitors 232, 234 or a first set of compliant capacitors extending along the longitudinal length of the angular displacement sensor 212, similar to embodiments described above. In addition, the angular displacement sensor 212 includes third and fourth compliant capacitors 236, 238 or a second set of compliant capacitors oriented orthogonally relative to the first and second compliant capacitors 232, 234. The third and fourth compliant capacitors 236, 238 may include the same structural characteristics as the first and second compliant capacitors 232, 234, but for their orientation relative to the first and second compliant capacitors 232, 234.

As in the embodiments described above, the first and second compliant capacitors 232, 234 may sense bending movement and provide data of a first angular displacement 260 in a first plane 270, the angular displacement 260 being measured between the first and second vectors 252, 254 defined by the first and second rigid members 216, 218. Likewise, the third and fourth compliant capacitors 236, 238 may sense bending movement of the angular displacement sensor 212 relative to a second angular displacement 262 defined within a second plane 272, the first plane 270 being orthogonal to the second plane 272. Similarly, the second angular displacement 262 may be measured and calculated between the first and second vectors 252', 254' defined by the first and second rigid members 216, 218 relative to their orientation in the second plane 272. The second plane 272 may be defined along the axis 224 of the angular displacement sensor 212 (co-axial with the first and second vectors 252', 254') and orthogonally oriented relative to a width dimension 244' of the third and fourth compliant capacitors 236, 238. Similarly, the first plane 270 may be defined along the axis 224 of the angular displacement sensor 212 and orthogonally oriented relative to a width dimension 244 of the first and second compliant capacitors 232, 234. With the arrangement of the depicted embodiment, the sensor system 210 may determine a first angular displacement relative to the first plane 270 and a second angular displacement relative to the second plane 272 via the corresponding respective first and second compliant capacitors 232, 234 and the third and fourth compliant capacitors 236, 238. The first, second, third and fourth compliant capacitors 232, 234, 236, 238 extend within the elongated structure of the angular displacement sensor 212 as described herein.

The third and fourth compliant capacitors 236, 238 may be formed similarly to the first and second compliant capacitors 232, 234, as set forth herein. For example, the third and fourth compliant capacitors 236, 238 may each include the outer and inner electrodes 38, 40 (not individually illustrated in FIG. 9B as shown in FIG. 2B) with the non-conductive dielectric layer 42 therebetween, as well as including a spring electrode 50 extending along or partially embedded in each of the outer and inner electrodes 38, 40 (see FIGS. 2A and 2B).

Figure 9C:
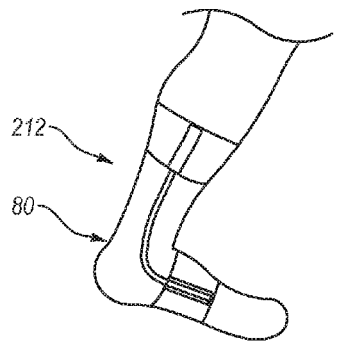
FIG. 9C is a side view of a sensor system coupled over an ankle joint, according to another embodiment of the present disclosure.

As depicted in FIG. 9C, the sensor system 210 of this embodiment may be positioned along an anatomical joint 80, such as an ankle joint. Such also may be employed with other anatomical joints 80 in the anatomy, such as a shoulder joint and a hip joint, and even the knee and elbow joints described herein. In another embodiment, the sensor system 210 may be employed along the neck and back of a user.

With respect to FIG. 10A, another embodiment of a sensor system 310, only partially showing a sensor portion, is provided. In this embodiment, the sensor system 310 may include an angular displacement sensor 312 including a single compliant capacitor (not shown) with a helical orientation about the center axis 324 or a pair of compliant capacitors 331 oriented in a cohelical fashion extending through the elongated structure 314 of the angular displacement sensor 312. Such helical compliant capacitors 331 may be in addition to, or instead of, first and/or second sets of compliant capacitors extending linearly and parallel through the elongated structure 314, as described above in other embodiments. Such helical compliant capacitors 331 may be sized and configured to sense torque or twisting in the angular displacement sensor 312 and provide angular displacement 361 about the axis 324 of the angular displacement sensor 312 relative to the orientation of the first and second rigid members (not shown in FIG. 10A) moved between a non-rotated position to one or more rotated positions. This rotational motion defines an angular displacement within a third plane (not shown), which is orthogonal to the planes 270 and 272 (illustrated in FIG. 9A) and which measures the torsion (e.g., torsional displacement) about axis 324. In such an arrangement, twisting in one direction induces a positive change in capacitance in one compliant capacitor and a negative change of capacitance in a second compliant capacitor, the differential measurement of which yields a value proportional to the angular displacement about the axis 324 within the third aforementioned plane. In the case of one single compliant capacitor, the positive change or negative change in capacitance can be used to determine angular displacement about the axis 324. With this arrangement, the sensor system 310 may include the helical compliant capacitors 331 extending with a helical or cohelical configuration through the elongated structure 314 and along the longitudinal length of the elongated structure 314. Further, the sensor system 310 may also include the first and second compliant capacitors 332, 334 and/or the third and fourth compliant capacitors 336, 338, set forth in some embodiments described above, including the spring electrode 50 (FIGS. 2A and 2B) positioned along each of the outer and inner electrodes of each compliant capacitor, as described herein. Such spring electrode 50 may also be integrated along each side of the helical compliant capacitors 331. Such helical compliant capacitors 331 may be formed with similar components as the first and second compliant capacitors 332, 334 such that each helical compliant capacitors 331 include the inner and outer electrodes with the elastomer dielectric layer therebetween. By incorporating helical or cohelical compliant capacitors 331 along with compliant capacitor pairs 332, 334 and 336, 338, angular displacement in three orthogonal planes may be measured. The helical or cohelical compliant capacitors 331 may be placed either on the outside of compliant capacitor sets 332/334 and 336/338 or on the inside, or between these compliant capacitor sets. Advantageously, the sensor system 310 of this embodiment may be employed over anatomical joints that may provide some rotation, such as, for example, the shoulder joint and the hip joint as well as the neck and back and, further, anatomical joints that provide bending movement in the first plane 270 and/or the second plane 272 (see FIGS. 2B, 9A, and 9B), as described herein. It is noted that the angular displacement about axis 324 may be used in conjunction with the angular displacements 260 and 262 in order to perform a calibration of a three-axis sensor system 314 that will allow for the measurement of the three aforementioned angular displacements that will be accurate over all possible deformations of the sensor system 310. In particular, the angular displacement about axis 324 can be used to compensate for errors in the measurement of angular displacements 260 and 262 induced by twisting of the sensor 314 about the axis 324. In this calibration, the raw output from the measurement of compliant capacitor pairs 331, 332, 334 and 336, 338 may be used in conjunction with an appropriate calibration procedure while the angular displacement sensor 312 is moved through its full range of motion throughout all three planes and curve fit to an appropriate multidimensional function.

In some embodiments, a calibration curve relates an output of the angular displacement sensor 312 in a single plane or multiple orthogonal planes to conventional systems of angle measurement, such as degrees or radians, and compensates for errors in angular displacement measurement resulting in twisting of the elongated structure 314 and cross talk of two or more compliant capacitors in orthogonal planes, which may result from imperfections in manufacturing measurement circuit design and construction.

Figure 10C:
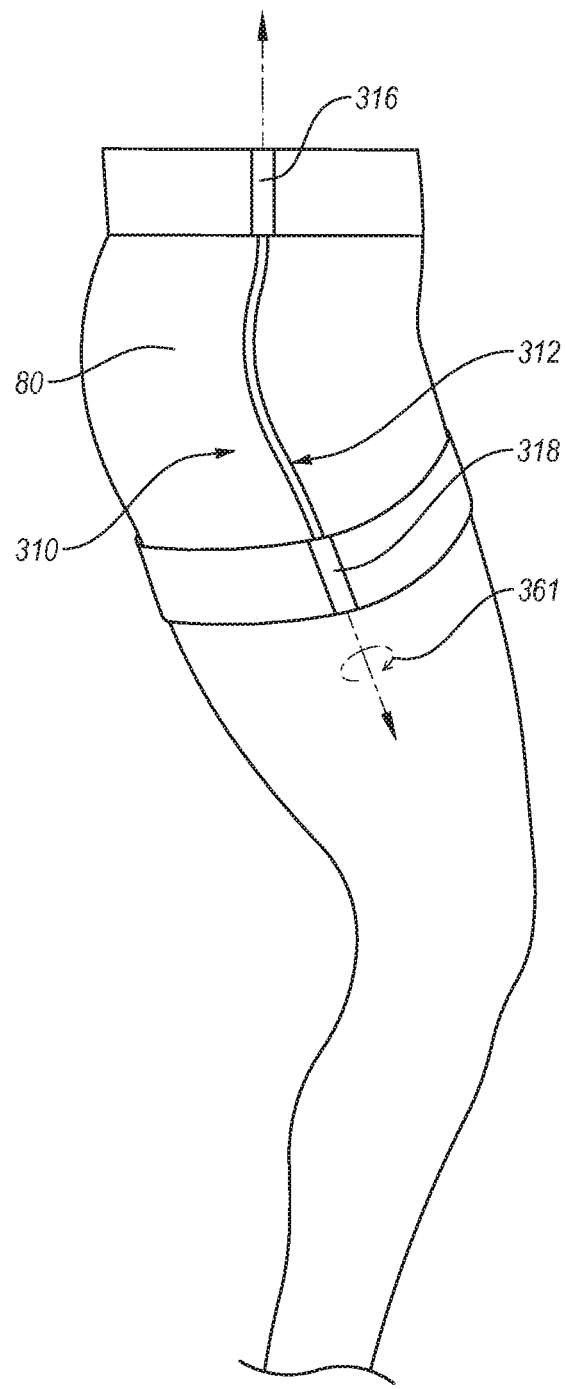
FIG. 10C is a side view of the sensor system coupled over a hip joint, according to another embodiment of the present disclosure.

For example, with respect to FIGS. 10B and 10C, the sensor system 310 described relative to FIG. 10A may be positioned adjacent anatomical joints 80, such as shoulder or hip joints, respectively depicted. In one embodiment, the first rigid member 316 may be positioned proximal the shoulder/hip joint and the second rigid member 318 may be positioned distal the shoulder/hip joint such that the angular displacement sensor 312 extends over and/or to the side of the shoulder/hip joint. With the sensor system 310 of this embodiment, the sensor system 310 may sense rotational movement about axis 324, between the first and second rigid members 316, 318, as well as bending movement relative to an angular displacement 260, 262 in a first plane 270 and a second plane 272 (see FIGS. 9A and 9B), as described herein. Further, the sensor system 310 of this embodiment may include all of the features and components discussed in the embodiments of the sensor system 10 described above, including being coupled to the interface device 20 with its various components (including the biofeedback device 110, memory 122, and micro-controller 114) for logging data 142 and transferring such data to a remote device 22 for further analysis (see FIGS. 5A and 7). In this manner, the user 84 may obtain useful data of the user's progress or decline of twisting and bending movement in the anatomical joints 80 of the user over one or more sessions of employing the sensor system 310.

As will be apparent to one of ordinary skill in the art, the various embodiments of the sensor system described herein may be employed with other portions of the human anatomy, such as, the various digits of the human anatomy as well as any other moving joint, appendage or portion of the human anatomy. Further, the sensor system may also be employed with robotic arms, mechanical positioning devices, and rotary actuators, or any other suitable structure that may be useful to analyze or obtain information from not only in, for example, the medical and physical therapy industries, but also industries involving sports and athletics, computer and gaming systems, the entertainment industry involving, theater, animation, computer generation imaging and so forth.

Figure 11:
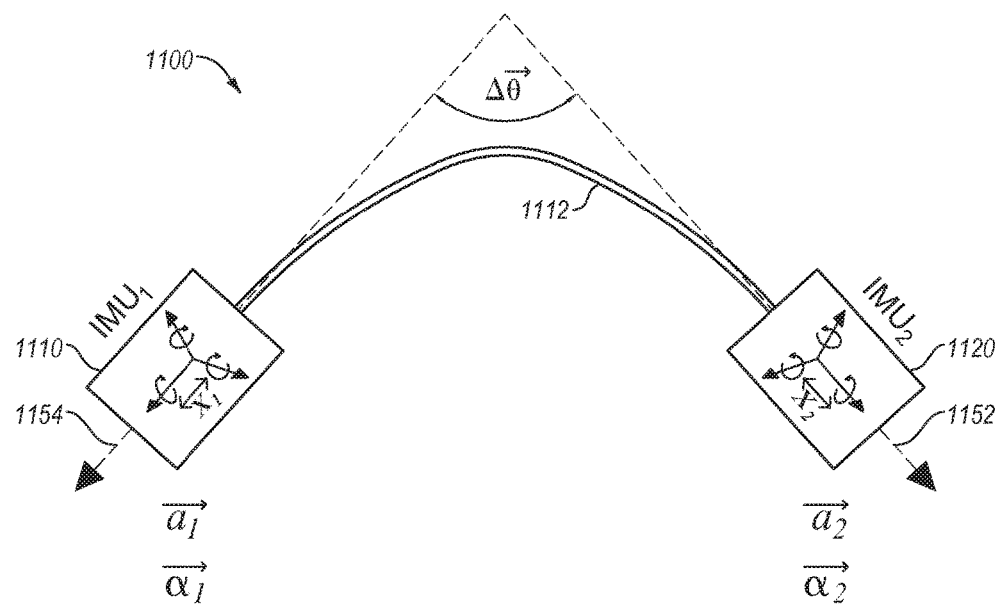
FIG. 11 is another embodiment of a sensor system for sensing angular displacement between two vectors, according to another embodiment of the present disclosure.

Referring to FIG. 11, another embodiment of the sensor system 1100 for sensing angular displacement between two vectors 1152, 1154 defined by rigid members is provided. The sensor system 1100 may include similar components as the sensor system 10 of FIG. 1A, the sensor system 210 of FIG. 9, or the sensor system 310 of FIG. 10A. The sensor system 1100 may include the angular displacement sensor 1112 (e.g., angular displacement sensor 12, angular displacement sensor 212, or angular displacement sensor 312), which may measure a single, two or three orthogonal angular displacement values, and one or more inertial measurement units (IMUs) 1110, 1120. The IMUs 1110, 1120 may include any combination of accelerometers, gyroscopes, global positioning system (GPS) units, and the like. As illustrated, the sensor system 1100 includes two IMUs 1110, 1120. The one or more IMUs may be coupled to one or more rigid members of the sensor system 1100. For example, the first IMU 1110 may be coupled to a first rigid member (e.g., first rigid member 16 of FIG. 1A) and the second IMU may be coupled to a second rigid member (e.g., second rigid member 18 of FIG. 1A). The angular displacement sensor 1112 may have rigid ends defined by the coordinate systems $X_1$ and $X_2$ and may measure an angular displacement vector (AO), where this vector is defined by three angular displacements in orthogonal planes. Each IMU 1110, 1120 measures acceleration vectors ($a_1$ and $a_2$) and angular velocity vectors ($\alpha_1$ and $\alpha_2$), respectively. In some embodiments, the axis of each IMU 1110, 1120 may be aligned with the angular displacement sensor end vectors 1152, 1154, respectively. Alternatively, the axis of each IMU 1110, 1120 may be offset with the angular displacement sensor end vectors 1152, 1154, respectively.

Figure 12:
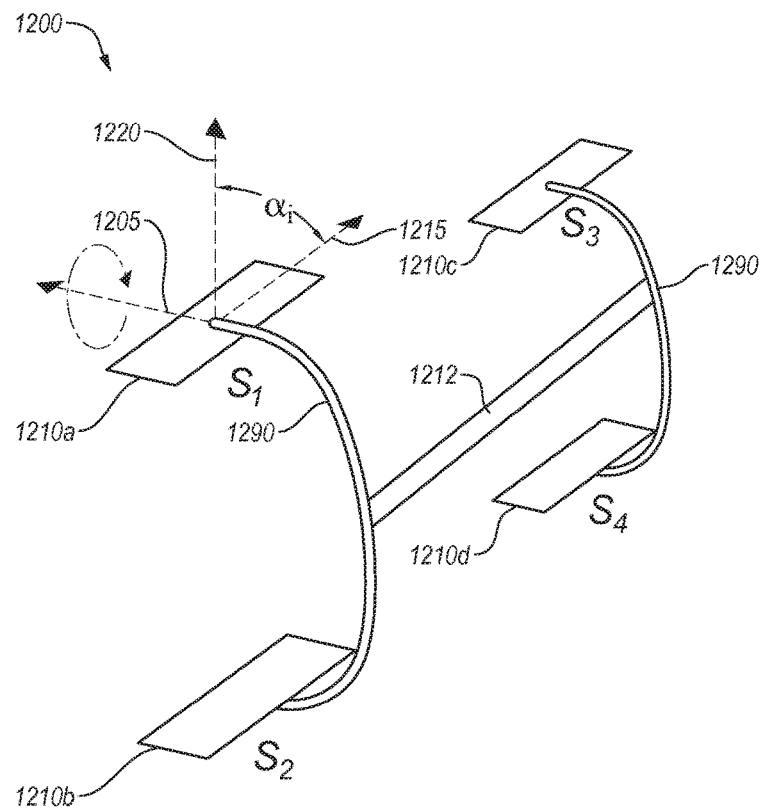
FIG. 12 illustrates another embodiment of a sensor system that includes two instrumented registration members that are coupled to an angular displacement sensor, in accordance with some embodiments.

FIG. 12 illustrates another embodiment of a sensor system 1200 that includes two instrumented registration members 1290 that are coupled to an angular displacement sensor 1212, in accordance with some embodiments. The sensor system 1200 may include similar components as the sensor system 10 of FIG. 1A, the sensor system 210 of FIG. 9, or the sensor system 310 of FIG. 10A. For example, the angular displacement sensor 1212 may be similar to the angular displacement sensor 12, angular displacement sensor 212, or angular displacement sensor 312, as described herein, and the registration members 1290 may be similar to the registration members 90 described herein. The angular displacement sensor 1212 is coupled between the two instrumented registration members 1290. The instrumented registration members 1290 are coupled to or otherwise include rotational sensors 1210a-d to measure an angle $\alpha_i$ between an axis 1215 of a registration member 1290 and a vector 1220 defined by a rotating member (not shown) that may rotate about axis 1205. The rotational sensors 1210a-d may also be angular sensors or a combination of rotational and angular sensors that measure the angle $\alpha_i$ between the axis 1215 and the vector 1220. As the rotating member rotates about the axis 1205, the angle $\alpha_i$ between the axis 1215 and the vector 1220 changes. Although four rotational sensors 1210a-d are illustrated in the depicted embodiment, in other embodiments, one or more such sensors may be used.

Figure 13:
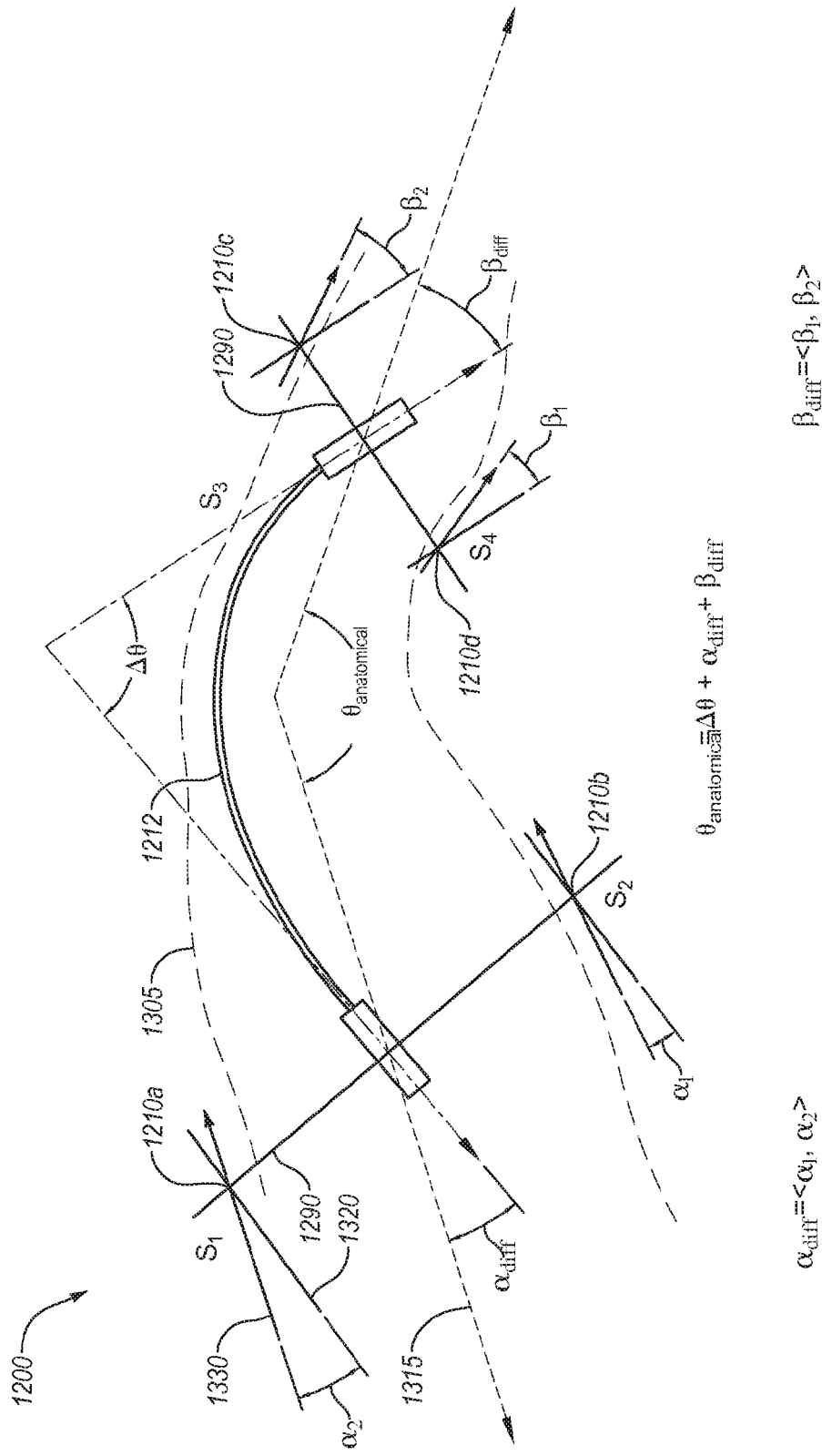
FIG. 13 illustrates another embodiment of a sensor system that includes one or more instrumented registration members that may be used to detect movement of a body part, in accordance with some embodiments.

FIG. 13 illustrates the sensor system of FIG. 12 in greater detail, which includes one or more instrumented registration members 1290 that may be used to detect movement of a body part 1305, in accordance with some embodiments. For the sake of illustration, the body part 1305 is depicted as a leg with a knee joint. The registration members 1290 may not align with an anatomical axis (dashed line) 1315 of the body part, which may result in an angle $\alpha_i$ and $\beta_i$ between an axis 1320 of the registration members 1290 and an axis 1330 of the rotational sensors 1210a-d. By taking the average of these values across each of the rotational sensors 1210a-d, the angular difference between the sensor axis 1330 and anatomical axis 1315 can be measured at both ends of the sensor system 1200. As illustrated, the sensor system 1200 includes four rotational sensors 1210a-d, with one rotational sensor attached on each end of two registration members 1290, though any number of rotational sensors 1210 may be used.

Figure 14:
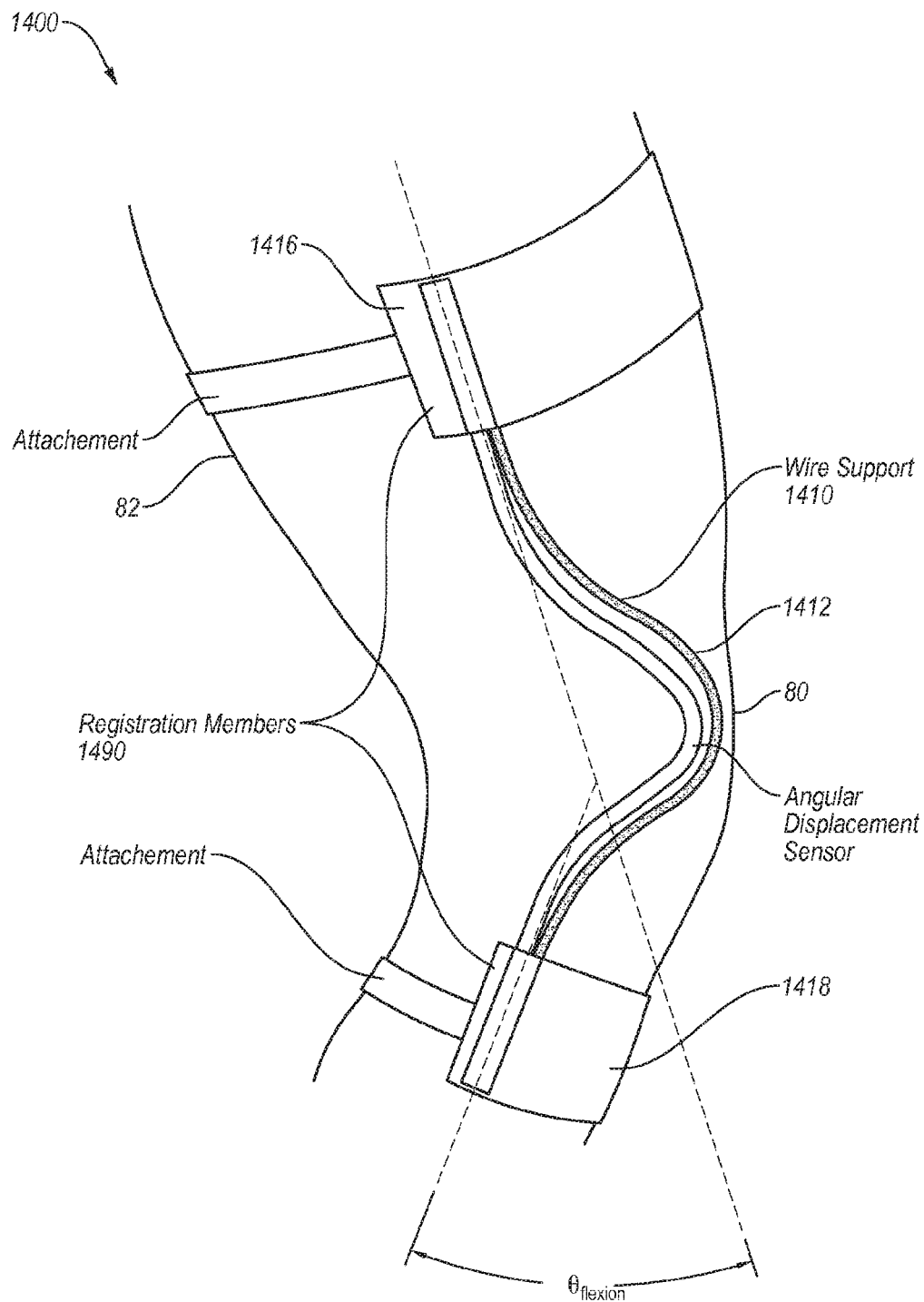
FIG. 14 is a side view of the sensor system, coupled over an anatomical joint, according to another embodiment of the present disclosure.

Now with reference to FIG. 14, a sensor system 1400 is depicted in use with an angular displacement sensor 1412 extending over an anatomical joint 80, such as a knee joint, with the first and second rigid members 1416, 1418 coupled to a leg 82 of a person, similar to the leg 82 as illustrated in FIG. 5A. The sensor system 1400 may include similar components as the sensor system 10 of FIG. 1A, the sensor system 210 of FIG. 9, or the sensor system 310 of FIG. 10A. The sensor system 1400 can also include one or more registration members 1490. In one embodiment, sensor system 1400 includes a rigid but flexible support 1410 (e.g., a wire support), which prevents the sensor system 1400 from sliding down the leg 82. The default position of the sensor 1412 may include a bend to facilitate a more comfortable brace. Support of this structure for the sensor 1412 may be facilitated by the support 1410.

In some embodiments, the first rigid member 1416 is configured to be removably fixed and positioned proximal the anatomical joint 80 and the second rigid member 1418 is configured to be removeably fixed and positioned distal the anatomical joint 80 such that the angular displacement sensor 1412 extends adjacently over the anatomical joint 80 to measure angular displacement of the anatomical joint 80.

Figure 15:
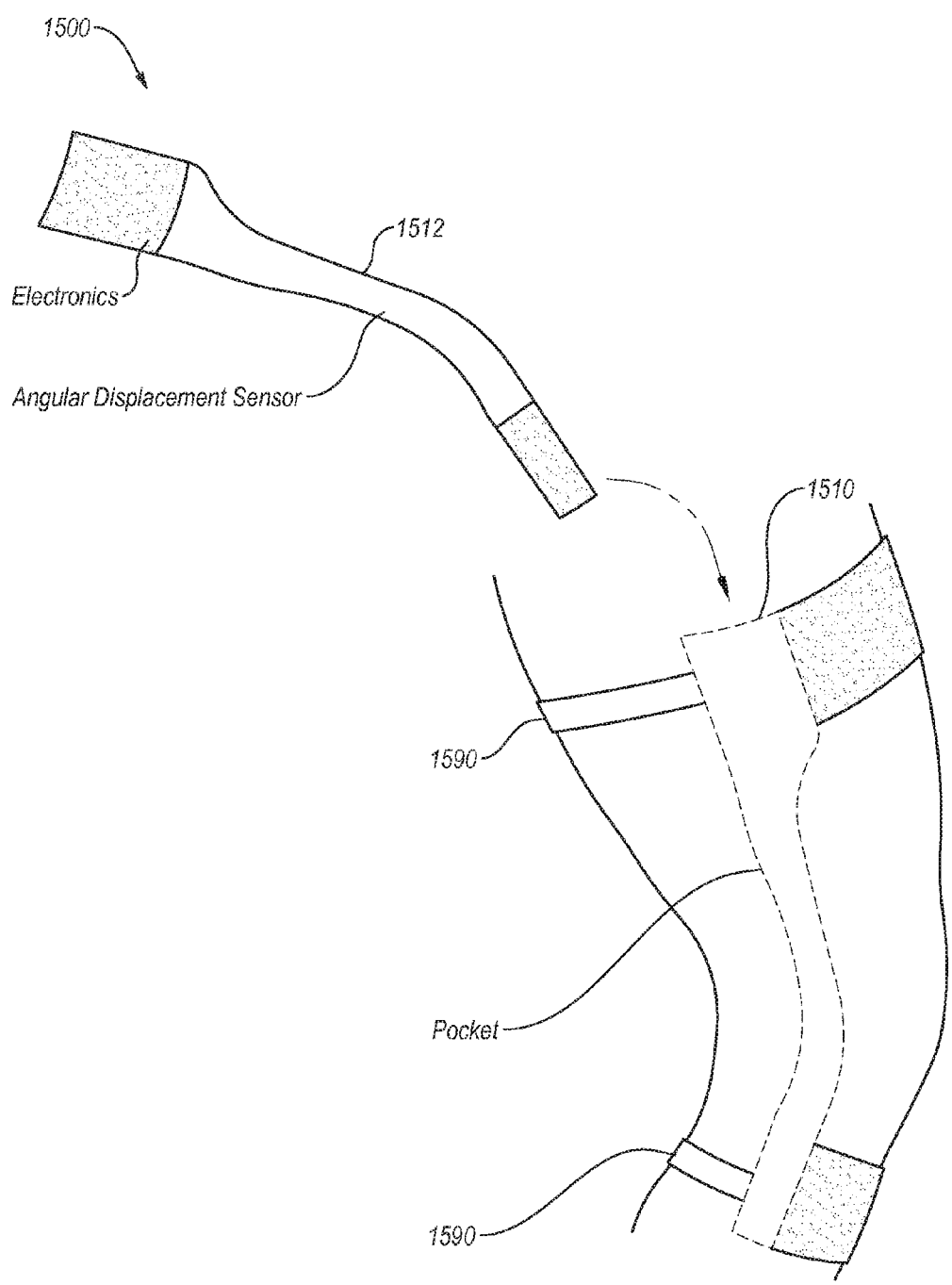
FIG. 15 illustrates a motion sensing system with a removable angular displacement sensor, in accordance with some embodiments.

FIG. 15 illustrates a motion sensing system 1500 with a removable angular displacement sensor 1512, in accordance with some embodiments. The motion sensing system 1500 may include similar components as the sensor system 10 of FIG. 1A, the sensor system 210 of FIG. 9, or the sensor system 310 of FIG. 10A. The motion sensing system 1500 may include one or more registration members 1590 and a pocket 1510 that receives a removable angular displacement sensor 1512. The removable angular displacement sensor 1512 may be similar to any of the angular displacement sensors described herein, such as angular displacement sensor 12, angular displacement sensor 212, and angular displacement sensor 312, which measures one, two or three orthogonal angular displacements. The motion sensing system 1500 may also include on or more IMU's as described herein. The removable angular displacement sensor 1512 may be slidably inserted into and removed from the pocket 1510. In some embodiments, the removable angular displacement sensor 1512 attaches to the motion sensing system 1500 via buttons, all-purpose straps (e.g., Velcro® straps) or by other means, such that the removable angular displacement sensor 1512 can be placed in different braces, garments or devices.

Figure 16:
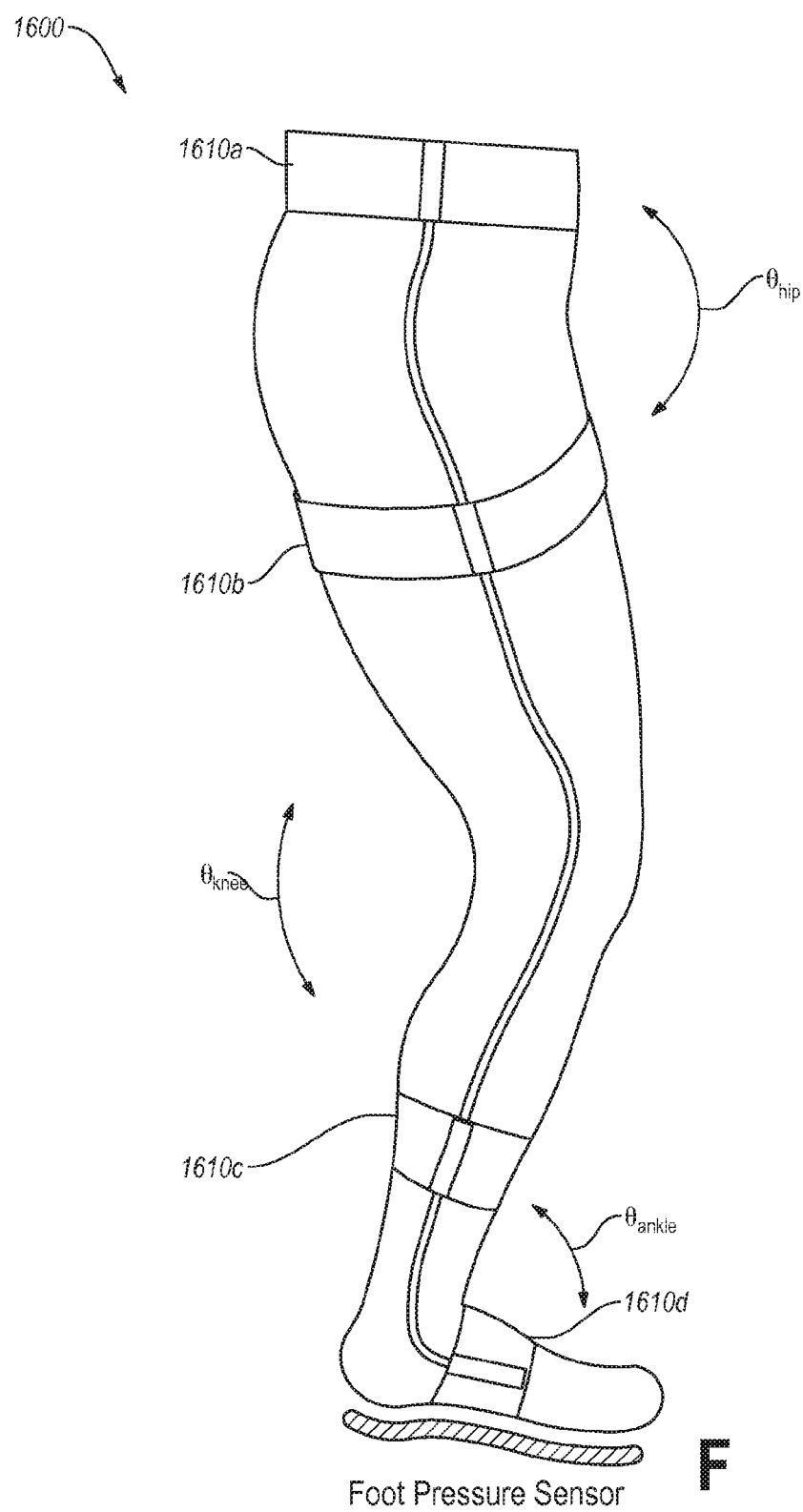
FIG. 16 illustrates a linked motion measurement system, in accordance with some embodiments.

FIG. 16 illustrates a linked motion measurement system 1600, in accordance with some embodiments. The linked motion measurement system 1600 may include similar components as the sensor system 10 of FIG. 1A, the sensor system 210 of FIG. 9, or the sensor system 310 of FIG. 10A. In addition, the linked motion measurement system 1600 may include multiple sensor systems 1610 located at different parts of a body. As illustrated, the linked motion measurement system 1600 includes four sensor systems 1610*a-d*. Each of the sensor systems 1610 may be linked together either wirelessly or via data cables to form a single motion measurement system. Alternatively, each of the sensor systems 1610 may be linked to a separate motion measurement system. Such data may be used to perform any type of data analysis for movements of the body. Example analysis can include inverse dynamics calculations to reconstruct muscle and joint forces and torques or for motion recognition.

In some embodiments, linked motion measurement system 1600 includes sensing systems that are not attached to a body. For example, the linked motion measurement system 1600 may include one or more cameras that may be used in conjunction with one or more of the sensor systems 1610 to detect motion. The linked motion measurement system 1600 may include a controller coupled to the one or more cameras. The controller may use the camera to detect the body and any movements of the body, as described herein.

A method of measuring movement of an anatomical joint of a user using a sensor system is also described. The sensor system may include similar components as the sensor system 10 of FIG. 1A, the sensor system 210 of FIG. 9, or the sensor system 310 of FIG. 10A. The sensor system may include an angular displacement sensor (e.g., angular displacement sensor 12, angular displacement sensor 212, or angular displacement sensor 312), as described herein.

The method includes providing an angular displacement sensor having an elongated flexible structure defining an axis extending along a longitudinal length of the elongated structure between a first end and a second end. The first end may be coupled to a first rigid member and the second end may be coupled to a second rigid member. The first rigid member may define a first vector and the second rigid member may define a second vector. The first and second vectors may extend substantially co-axial with the axis of the elongated structure when the elongated structure is in a substantially linear non-bent position.

The method can also include positioning the first rigid member to the user at a proximal position of the anatomical joint. The method can further include positioning the second rigid member to the user at a distal position of the anatomical joint. The elongated structure of the angular displacement sensor may adjacently extend over the anatomical joint of the user with the first and second rigid members positioned to the user in a substantially fixed manner.

The method can also include measuring an angular displacement in one or more orthogonal planes that is defined between the first and second vectors when the elongated structure is moved from the substantially linear non-bent position to a bent position via a movement of the anatomical joint by the user. In some embodiments, measuring the angular displacement in one or more orthogonal planes includes measuring with a differential measuring circuit associated with the angular displacement sensor. The angular displacement sensor may include at least one compliant strain sensor having a width extending along the longitudinal length of the elongated structure, as described herein. In further embodiments, measuring the angular displacement in one or more orthogonal planes includes measuring a change in the angular displacement in one or more planes between the first and second vectors defined by the respective first and second rigid members. In some embodiment, the method may also include generating biofeedback signals to a user based on the measured angular displacement meeting input parameters with at least one of an audible notification, a visual notification, and a vibrational tactile notification.

The method may also include performing a calibration of the angular displacement sensor that accounts for misalignment between the first and second rigid members and the anatomical axis of the anatomical joint being measured.

In some embodiments, the method includes storing data in an interface device coupled to the angular displacement sensor. The method may also include transferring the data to a remote device.

Figure 17:
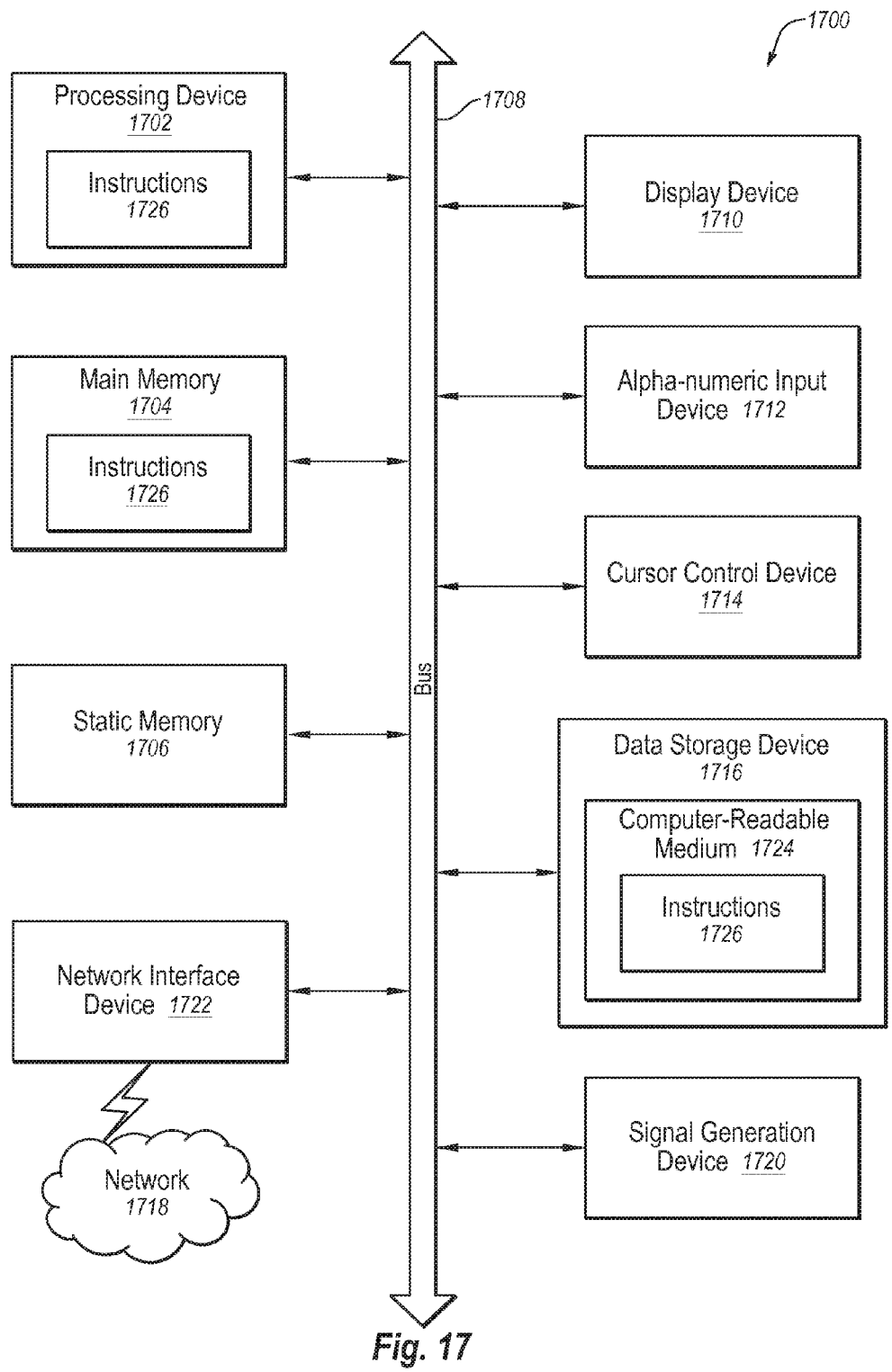
FIG. 17 illustrates a diagrammatic representation of a machine in the example form of a computer system, in accordance with some embodiments.

FIG. 17 illustrates a diagrammatic representation of a machine in the example form of a computer system 1700 within which a set of instructions, for causing the machine to perform any one or more of the methodologies discussed herein, may be executed. The computer system 1700 may correspond to the interface device 20 of FIGS. 1A, 5A and 7, remote device 22 of FIGS. 1A, 5A and 7, personal computer 102 of FIG. 5A, micro-controller 114 that executes the control and analysis software 124. The computer system 1700 may correspond to an IMU or a computer system in communication with an IMU, as described herein. In embodiments of the present invention, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computer system 1700 includes a processing device 1702, a main memory 1704 (e.g., read-only memory (ROM), flash memory, dynamic random access memory (DRAM) such as synchronous DRAM (SDRAM), a static memory 1706 (e.g., flash memory, static random access memory (SRAM), etc.), and a secondary memory 1716 (e.g., a data storage device), which communicate with each other via a bus 1708.

The processing device 1702 represents one or more general-purpose processors such as a microprocessor, central processing unit, or the like. The term "processing device" is used herein to refer to any combination of one or more integrated circuits and/or packages that include one or more processors (e.g., one or more processor cores). Therefore, the term processing device encompasses a microcontroller, a single core CPU, a multi-core CPU and a massively multi-core system that includes many interconnected integrated circuits, each of which may include multiple processor cores. The processing device 1702 may therefore include multiple processors. The processing device 1702 may include a complex instruction set computing (CISC) microprocessor, reduced instruction set computing (RISC) microprocessor, very long instruction word (VLIW) microprocessor, processor implementing other instruction sets, or processors implementing a combination of instruction sets. The processing device 1702 may also be one or more special-purpose processing devices such as an application specific integrated circuit (ASIC), a field programmable gate array (FPGA), a digital signal processor (DSP), network processor, or the like.

The computer system 1700 may further include one or more network interface devices 1722 (e.g., NICs). The computer system 1700 also may include a video display unit 1710 (e.g., a liquid crystal display (LCD) or a cathode ray tube (CRT)), an alphanumeric input device 1712 (e.g., a keyboard), a cursor control device 1714 (e.g., a mouse), and a signal generation device 1720 (e.g., a speaker).

The secondary memory 1716 may include a machine-readable storage medium (or more specifically a computer-readable storage medium) 1724 on which is stored one or more sets of instructions 1754 embodying any one or more of the methodologies or functions described herein. The instructions 1754 may also reside, completely or at least partially, within the main memory 1704 and/or within the processing device 1702 during execution thereof by the computer system 1700; the main memory 1704 and the processing device 1702 also constituting machine-readable storage media.

While the computer-readable storage medium 1724 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine that cause the machine to perform any one or more of the methodologies of the present embodiments. The term "computer-readable storage medium" shall accordingly be taken to include, but not be limited to, non-transitory media such as solid-state memories, and optical and magnetic media.

The modules, components and other features described herein can be implemented as discrete hardware components or integrated in the functionality of hardware components such as ASICS, FPGAs, DSPs or similar devices. In addition, the modules can be implemented as firmware or functional circuitry within hardware devices. Further, the modules can be implemented in any combination of hardware devices and software components, or only in software.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "identifying", "probing", "establishing", "detecting", "modifying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specially constructed for the required purposes, or it may comprise a general purpose computer system selectively programmed by a computer program stored in the computer system. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic disk storage media, optical storage media, flash memory devices, other type of machine-accessible storage media, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear as set forth in the description above. In addition, the present embodiments are not described with reference to any particular programming language. It will be appreciated that a variety of programming languages may be used to implement the teachings of the embodiments as described herein.

It is to be understood that the above description is intended to be illustrative, and not restrictive. Many other embodiments will be apparent to those of skill in the art upon reading and understanding the above description. Although the present embodiments has been described with reference to specific examples, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. An apparatus comprising:
   an elongated structure extending between a first end and a second end, the elongated structure being compliant material that is bendable from a linear, non-bent position to multiple bendable positions of an anatomical joint;
   a first compliant capacitor layer embedded at least partially within and extending from the first end to the second end along a longitudinal length of the elongated structure;
   a second compliant capacitor aligned perpendicular to the first compliant capacitor and embedded at least partially within and extending from the first end to the second end along the longitudinal length of the elongated structure; and
   a registration member coupled to the first end and the second end of the elongated structure, wherein the registration member is to position the first end and the second end of the elongated structure proximal and distal the anatomical joint respectively, wherein a first capacitance of the first compliant capacitor and a second capacitance of the second compliant capacitor are measured to sense angular displacement of the anatomical joint.

2. The apparatus of claim 1, wherein the registration member further comprises:
   a first attachment unit to secure the first end of the elongated structure to a first human body part proximal the anatomical joint; and
   a second attachment unit to secure the second end of the elongated structure to a second human body part distal the anatomical joint.

3. The apparatus of claim 1, wherein the registration member comprises a hook and loop fastener.

4. The apparatus of claim 1, wherein the registration member comprises a strap with a fastener.

5. The apparatus of claim 1, wherein the registration member is integrated with an article of clothing.

6. The apparatus of claim 1, wherein the first compliant capacitor comprises:
   a first conductive layer embedded at least partially within and extending from the first end to the second end along the longitudinal length of the elongated structure to form a first electrode of the first compliant capacitor;
   a second conductive layer embedded at least partially within and extending from the first end to the second end along the longitudinal length to form a second electrode of the first compliant capacitor; and
   a first elastomer dielectric layer extending between the first conductive layer and the second conductive layer.

7. The apparatus of claim 1, wherein the first end of the elongated structure defines a first vector corresponding with an axis, and wherein the second end of the elongated structure defines a second vector corresponding with the axis, and wherein the angular displacement is determined in a first plane between the first vector and the second vector, the first plane extending along the longitudinal length and extending orthogonal through a width of the first compliant capacitor.

8. The apparatus of claim 1, further comprising
   a third compliant capacitor aligned parallel to the first compliant capacitor, wherein the third compliant capacitor is embedded at least partially within and extending from the first end to the second end along the longitudinal length of the elongated structure, wherein the first capacitance of the first compliant capacitor and a third capacitance of the third compliant capacitor are measured to sense the angular displacement of the anatomical joint with respect to a first plane.

9. The apparatus of claim 1, further comprising
   a fourth compliant capacitor aligned perpendicular to the first compliant capacitor and parallel to the second compliant capacitor, wherein the fourth compliant capacitor is embedded at least partially within and extending from the first end to the second end along the longitudinal length of the elongated structure, wherein the second capacitance of the second compliant capacitor and a fourth capacitance of the fourth compliant capacitor are measured to sense the angular displacement of the anatomical joint with respect to a second plane.

10. A sensor system comprising:
    an angular displacement sensor comprising:
       an elongated structure extending between a first end and a second end, the elongated structure being compliant material that is bendable from a linear, non-bent position to multiple bendable positions of an anatomical joint; and
       a first compliant capacitor layer embedded at least partially within and extending from the first end to the second end along a longitudinal length of the elongated structure; and
       a registration member coupled to the first end and the second end of the elongated structure, wherein the registration member is to position the first end and the second end of the elongated structure proximal and distal the anatomical joint respectively, wherein a first capacitance of the first compliant capacitor is measured to sense an angular displacement of the anatomical joint;

a circuit coupled to the first compliant capacitor, the circuit to measure the first capacitance of the first compliant capacitor to sense bending movement of the elongated structure;

a memory device coupled with the circuit, the memory device to store data indicative of the first capacitance; and a transmitter coupled to the memory device, the transmitter to wirelessly transmit the data indicative of the first capacitance to a remote device.

11. The sensor system of claim 10, wherein the registration member further comprises:

a first attachment unit to secure the first end of the elongated structure to a first human body part proximal the anatomical joint; and a second attachment unit to secure the second end of the elongated structure to a second human body part distal the anatomical joint.

12. The sensor system of claim 10, wherein the registration member comprises a hook and loop fastener.

13. The sensor system of claim 10, wherein the registration member is integrated with an article of clothing.

14. The sensor system of claim 10, wherein the angular displacement sensor further comprises a second compliant capacitor aligned parallel to the first compliant capacitor, wherein the second compliant capacitor is embedded at least partially within and extending from the first end to the second end along the longitudinal length of the elongated structure, wherein the first capacitance of the first compliant capacitor and a second capacitance of the second compliant capacitor are measured to sense the angular displacement of the anatomical joint.

15. The sensor system of claim 10, wherein the first end of the elongated structure defines a first vector corresponding with an axis, and wherein the second end of the elongated structure defines a second vector corresponding with the axis, and wherein the angular displacement in a first plane is determined between the first vector and the second vector, the first plane extending along the longitudinal length and extending orthogonal through a width of the first compliant capacitor.

* * * * *